(12) United States Patent
Agazie et al.

(10) Patent No.: US 9,932,288 B2
(45) Date of Patent: Apr. 3, 2018

(54) CHEMICAL COMPOUND FOR INHIBITION OF SHP2 FUNCTION AND FOR USE AS AN ANTI-CANCER AGENT

(71) Applicant: West Virginia University, Morgantown, WV (US)

(72) Inventors: Yehenew Agazie, Morgantown, WV (US); Zachary Hartman, Morgantown, WV (US)

(73) Assignee: West Virginia University, Morgantown, WV (US)

(*) Notice: Subject to any disclaimer, the term of this patent is extended or adjusted under 35 U.S.C. 154(b) by 0 days.

(21) Appl. No.: 15/371,699

(22) Filed: Dec. 7, 2016

(65) Prior Publication Data

US 2017/0166510 A1 Jun. 15, 2017

Related U.S. Application Data

(60) Provisional application No. 62/265,084, filed on Dec. 9, 2015.

(51) Int. Cl.
| | |
|---|---|
| C07C 57/34 | (2006.01) |
| C07C 51/09 | (2006.01) |
| C12N 5/09 | (2010.01) |
| G01N 33/50 | (2006.01) |

(52) U.S. Cl.
CPC .............. *C07C 57/34* (2013.01); *C07C 51/09* (2013.01); *C12N 5/0693* (2013.01); *G01N 33/5008* (2013.01); *C12N 2501/01* (2013.01); *C12N 2501/11* (2013.01); *C12N 2501/115* (2013.01); *C12N 2501/33* (2013.01); *C12N 2501/91* (2013.01); *G01N 2333/916* (2013.01)

(58) Field of Classification Search
CPC ............................. C07C 57/34; A61K 31/192
See application file for complete search history.

(56) References Cited

U.S. PATENT DOCUMENTS

| | | | |
|---|---|---|---|
| 6,537,725 | B2 | 3/2003 | Kunita |
| 7,547,760 | B2 | 6/2009 | Agazie et al. |
| 2015/0152123 | A1 | 6/2015 | Zhou et al. |

OTHER PUBLICATIONS

International Search Report and Written Opinion for PCT/US2016/65318 dated Feb. 28, 2017.
Feng, Gen-Sheng et al., SH2-Containing Phosphotyrosine Phosphatase as a Target of Protein-Tyrosine Kinases, Science, New Series, 1993, 1607-1611, vol. 259, No. 5101, American Association for the Advancement of Science.
Hof, P. et al., Crystal Structure of the Tyrosine Phosphatase SHP-2, Cell, 1998, 441-450, vol. 92, Cell Press.
Bennett, A.M. et al., Multiple Requirements for SHPTP2 in Epidermal Growth Factor-Mediated Cell Cycle Progression, Molecular and Cellular Biology, 1996, 1189-1202, vol. 16, No. 3, American Society for Microbiology.
Saxton, T.M. et al., The SH2 Tyrosine Phosphatase Shp2 is required for mammalian limb development, Nature America Inc., 2000, 420-423, vol. 24, http://genetics.nature.com.
Saxton, T.M. et al., Abnormal mesoderm patterning in mouse embryos mutant for the SH2 tyrosine phosphatase Shp-2, 1997, The EMBO Journal, 2352-2364, vol. 16, No. 9.
O'Reilly, A.M. et al., Activated Mutants of SHP-2 Preferentially Induce Elongation of Xenopus Animal Caps, Molecular and Cellular Biology, 2000, 299-311, vol. 20, No. 1, American Society for Microbiology.
Tartaglia, M. et al., Somatic PTPN11 Mutations in Childhood Acute Myeloid Leukaemia, British Journal of Haematology, 2005, 333-339, vol. 129, Blackwell Publishing Ltd.
Tartaglia, M. et al., Mutations in PTPN11, encoding the protein tyrosine phosphatase SHP-2, cause Noonan syndrome, Nature Genetics, 2001, 465-468, vol. 29, Nature Publishing Group.
Tartaglia, M. et al., Somatic mutations in PTPN11 in juvenile myelomonocytic leukemia, myelodysplastic syndromes and acute myeloid leukemia, Nature Genetics, 2003, 148-150 and 464, vol. 34, No. 2, Nature Publishing Group.
Cunnick, J.M. et al., Requirement of SHP2 Binding to Grb2-associated Binder-1 for Mitogen-activated Protein Kinase Activation in Response to Lysophosphatidic Acid and Epidermal Growth Factor, The Journal of Biological Chemistry, 2000, 13842-13848, vol. 275, No. 18, The American Society for Biochemistry and Molecular Biology, Inc.
Hadari, Y.R., et al., Binding of Shp2 Tyrosine Phosphatase to FRS2 is Essential for Fibroblast Growth Factor-Induced PCT12 Cell Differentiation, Molecular and Cellular Biology, 1998, 3966-3973, vol. 18, No. 7, American Society of Microbiology.
Kuhne, M.R. et al., The Insulin Receptor Substrate 1 Associates with SH2-containing Phosphotyrosine Phosphatase Syp, The Journal of Biological Chemistry, 1993, 11479-11481, vol. 268, No. 16, The American Society for Biochemistry and Molecular Biology, Inc.
Lechleider, R.J., Activation of the SH2-containing Phosphotyrosine Phosphatase Sh-PTP2 by its Binding Site, Phosphotyrosine 1009, on the Human Platelet-derived Growth Factor Receptor β, The Journal of Biological Chemistry, 1993, 21478-21481, vol. 268, No. 29, The American Society for Biochemistry and Molecular Biology, Inc.

(Continued)

*Primary Examiner* — Sudhakar Katakam
(74) *Attorney, Agent, or Firm* — Buchanan Ingersoll & Rooney PC

(57) ABSTRACT

This invention provides a compound that is 4,4'-(4'-Carboxy)-4-nonyloxy-[1,1'-biphenyl]-3,5-diyl)dibutanoic acid (CNBDA), derivative compounds of CNBDA, and pharmaceutical compositions thereof. The derivative compounds of CNBDA have one or more of the following substitutions (a) replacement of one or both of the carboxylic acid groups of the CNBDA compound with an organic acid group having 1-3, or 5-30, or more carbon atoms in chain length, wherein the carbon atom chains are either saturated, partially saturated, or unsaturated with respect to the carbon to carbon bonding, (b) replacement of the carboxylic groups of (a) with a phosphate, a sulphate, an amide, a hydroxyl, an aldehyde, or a halide group, and (c) replacement of the nonane group with an alkane having a carbon chain length of 1-8 or 10-30, or more carbon atoms. A method of treating a patient having cancer is provided.

9 Claims, 11 Drawing Sheets

(56) References Cited

OTHER PUBLICATIONS

Schaeper, U., Coupling of Gab1 to c-Met, Grb2, and Shp2 Mediates Biological Responses, The Journal of Cell Biology, 2000, 1419-1432, vol. 149, No. 7, The Rockefeller University Press.

Tomic, S. et al., Association of SH2 Domain Protein Tyrosine Phosphatases with the Epidermal Growth Factor Receptor in Human Tumor Cells, Phosphatidic Acid Activates Receptor Dephosphorylation by PTP1C, The Journal of Biological Chemistry, 1995, 21277-21284, vol. 270, No. 36, The American Society for Biochemistry and Molecular Biology, Inc.

Bentires-Alj, M., et al., Activating Mutations of the Noonan Syndrome-Associated SHP2/PTPN11 Gene in Human Solid Tumors adn Adult Acute Myelogenous Leukemia, Cancer Research, 2004, 8816-8820, vol. 64.

Mohi, M. G. et al., Prognostic, therapeutic, and mechanistic implications of a mouse model of leukemia evoked by Shp2 (PTPN11) mutations, Cancer Cell, 2005, 179-191, vol. 7, Elsevier Inc.

Araki, T. et al., Mouse model of Noonan syndrome reveals cell type—and gene dosage—dependent effects of Ptpn11 mutation, Nature Medicine, 2004, 849-857, vol. 10, No. 8, Nature Publishing Group.

Flint, A. J. et al., "Substrate-Trapping" Mutants to Identify Physiological Substrates of Protein Tyrosine Phosphatases, Proceedings of the National Academy of Sciences of the United States of America, 1997, 1680-1685, vol. 94, No. 5, National Academy of Sciences.

Merritt, R., et al., Mutation of Thr466 in SHP2 abolishes its phosphatase activity, but provides a new substrate-trapping mutant, Biochimica et Biophysica Acta, 20016, 45-56, vol. 1763, Elsevier.

Frearson, J.A. et al., The Phosphotyrosine Phosphatase SHP-2 Participates in a Multimeric Signaling Comlex and regulates T Cell Receptor (TCR) coupling to the Ras/Mitogen-activated Protein Kinase (MAPK) Pathway in Jurkat T Cells, J. Exp. Med, 1998, 1417-1426, vol. 187, No. 9, The Rockefeller University Press.

Agazie Y.M. et al, Molecular Mechanism for a Role of SHP2 in Epidermal Growth Factor Receptor Signaling, Molecular and Cellular Biology, 2003, 7875-7886, vol. 23, No. 21, American Society for Microbiology.

Zhou, X. et al., Molecular Mechanism for SHP2 in Promoting HER2-induced Signaling and Transformation, The Journal of Biological Chemistry, 2009, 12226-12234, vol. 284, No. 18, The American Society for Biochemistry and Molecular Biology, Inc.

Burks, J. et al., Modulation of a-catenin Tyr phosphorylation by SHP2 positively effects cell transformation induced by the constitutively active FGFR3, Oncogene, 2006, 7166-7179, vol. 25, Nature Publishing Group.

Zhang, S.Q. et al., Shp2 Regulates Src Family Kinase Activity and Ras/Erk Activation by Controlling Csk Recruitment, Molecular Cell, 2004, 341-355, vol. 13, Cell Press.

Agazie, Y.M. et al., The phosphotyrosine phosphatase SHP2 is a critical mediator of transformation induced by the oncogenic fibroblast growth factor receptor 3, Oncogene, 2003, 6909-6918, vol. 22, Nature Publishing Group.

Hakak, Y. et al., Shp-2 mediates v-Src-induced morphological changes and activation of the anti-apoptotic protein kinase Akt, Oncogene, 2000, 3164-3171, vol. 19, Macmillan Publishers Ltd.

Aceto, N. et al., Tyrosine phosphatase SHP2 promotes breast cancer progression and maintains tumor-initiating cells via activation of key transcription factors and a positive feedback signaling loop, Nature Medicine, 2012, 529-538, vol. 18, No. 4, Nature America, Inc.

Ren, Y. et al., Critical Role of Shp2 in Tumor Growth Involving Regulation of c-Myc, Genes & Cancer, 2011, 994-1007, vol. 1, No. 10, The Author(s).

Zhou, X-D et al., Inhibition of SHP2 leads to mesenchymal to epithelial transition in breast cancer cells, Cell Death and Differentiation, 2008, 988-996, vol. 15, Nature Publishing Group.

Deb, T.B. et al., A Common Requirement for the Catalytic Activity and Both SH2 Domains of SHP-2 in Mitogen-activated Protein (MAP) Kinase Activation by the ErbB Family of Receptors, The Journal of Biological Chemistry, 1998, 16643-16646, vol. 273, No. 27.

Ahmed, Z. et al., Direct binding of Grb2 SH3 domain to FGFR2 regulates SHP2 function, Cellular Signalling, 2010, 23-33, vol. 22, Elsevier.

Ahmed, Z. et al., Grb2 controls phosphorylation of FGFR2 by inhibiting receptor kinase and Shp2 phosphatase activity, The Journal of Cell Biology, 2013, 493-504, vol. 200, No. 4, The Rockefeller University Press.

Li, J. et al., Hepatocyte growth factor (HGF) signals through SHP2 to regulate primary mouse myoblast proliferation, Experimental Cell Research, 2009, 2284-2292, vol. 315, Elsevier.

Mali, R.S. et al., Role of SHP2 phosphatase in KIT-induced transformation: identification of SHP2 as a druggable target in diseases involving oncogenic KIT, Blood Journal, 2012, 2669-2679, vol. 120, No. 13.

Miura, K., et al., Involvement of EphA2-mediated tyrosine phosphorylation of Shp2 in Shp2-regulated activation of extracellular signal-regulated kinase, Oncogene, 2013, 5292-5301, vol. 32, Macmillan Publishers Limited.

Muenst, S. et al., Src homology phosphotyrosyl phosphatase-2 expression is an independent negative prognostic factor human breast cancer, Histopathology, 2013, 74-82, vol. 63, John Wiley & Sons Ltd.

Zhou, X. et al., SHP2 is up-regulated in breast cancer cells and in infiltrating ductal carcinoma of the breast, implying its involvement in breast oncogenesis, Histopathology, 2008, 389-402, vol. 53, The Authors. Journal Compilation, Blackwell Publishing Limited.

Hara, M. et al, Interleukin-2 potentiation of cetuximab antitumor activity for epidermal growth factor receptor-overexpressing gastric cancer xenografts through antibody-dependent cellular cytotoxicity, Cancer Sci, 2008, 1471-1478, vol. 99, No. 7, Japanese Cancer Association.

Hognason, T. et al., Epidermal growth factor receptor induced apoptosis: potentiation by inhibition of Ras signaling, FEBS Letters, 2001, 9-15, vol. 491, Elsevier Science B. V.

Morris, G.M. et al., AutoDock4 and AutoDockTools4: Automated Docking with Selective Receptor Flexibility, J. Comput Chem., 2009, 2785-2791, vol. 30, Wiley Periodicals, Inc.

Ciardiello, F. et al., Antitumor Effect and Potentiation of Cytotoxic Drugs Activity in Human Cancer Cells by ZD-1839 (Iressa), an Epidermal Growth Factor Receptor-selective Tyrosine Kinase Inhibitor, Clinical Cancer Research, 2000, 2053-2063, vol. 6.

Maa, M.C et al., Potentiation of Epidermal Growth Factor Receptor-Mediated Oncogenesis by c-Src:Implications for the Etiology of Multiple Human Cancers, Proceedings of the National Academy of Sciences of the United States of America, 1995, 6981-6985, vol. 92, No. 15, National Academy of Sciences.

Bentires-Alj, M., et al., A role for the scaffolding adapter GAB2 in breast cancer, Nature Medicine, 2006, 114-121, vol. 12, No. 1, Nature Publishing Group.

Debnath, J. et al., Morphogenesis and oncogenesis of MCF-10A mammary epithelial acini grown in three-dimensional basement membrane cultures, Methods, 2003, 256-268, vol. 30, Elsevier.

Engelmann, K. et al., MCF7 Side Population Cells with Characteristics of Cancer Stem/Progenitor Cells Express the Tumor Antigen MUC1, Cancer Res, 2008, 2419-2426, vol. 68 No. 7, www.aacrjournals.org.

Fillmore, C.M. et al, Human breast cancer cell lines contain stem-like cells that self-renew, give rise to phenotypically diverse progeny and survive chemotherapy, Breast Cancer Research, 2008, 1-13, vol. 10, No. 2.

CHEMICAL COMPOUND FOR INHIBITION OF SHP2 FUNCTION AND FOR USE AS AN ANTI-CANCER AGENT

CROSS-REFERENCE TO RELATED APPLICATION

This utility patent application claims the benefit of co-pending U.S. Provisional Patent Application Ser. No. 62/265,084, filed on Dec. 9, 2015. The entire contents of U.S. Provisional Patent Application Ser. No. 62/265,084 is incorporated by reference into this utility patent application as if fully written herein.

STATEMENT REGARDING FEDERALLY SPONSORED RESEARCH OR DEVELOPMENT

None

BACKGROUND OF THE INVENTION

1. Field of the Invention

This invention refers to production of a synthetic compound termed 4,4'-(4'-Carboxy)-4-nonyloxy-[1,1'-biphenyl]-3,5-diyl)dibutanoic acid (hereinafter referred to as "CNBDA"), and compounds that are derivatives thereof, that inhibit the function of the Src homology phosphotyrosyl phosphatase 2 (SHP2). In addition, the current invention relates to the use of CNBDA as an anti-cancer agent.

2. Description of the Background Art

The Src homology phosphotyrosyl phosphatase 2 (SHP2) is an enzyme that catalyzes dephosphorylation reactions on proteins that bear phosphotyrosine. Structurally, SHP2 has two tandemly-arranged Src homology-2 (SH2) domains in the N-terminal region, a phosphotyrosyl phosphatase (PTP) domain in the C-terminal region and tyrosine phosphorylation sites in the extreme C-terminal tail [1, 2]. The SH2 domains mediate interaction with tyrosine phosphorylated proteins while the PTP domain catalyzes dephosphorylation reactions [3-6]. Specific SH2 domain-mediated interactions and the discriminating capability of the PTP domain confer SHP2 selectivity. The activity of SHP2 is regulated by an intramolecular conformational switch where it assumes a "closed conformation" when inactive and an "open conformation" when active. In the closed conformation, the N-SH2 domain interacts with the PTP domain, physically impeding substrate binding. Engagement of the N-SH2 domain relieves the PTP domain and renders the enzyme active [2]. Mutation of residues that mediate the closed conformation [7] leads to a constitutively active SHP2 found in some human diseases, including Noonan Syndrome and certain leukemia [8-10]. SH2 domain-mediated interaction of SHP2 with Tyr-phosphorylated proteins particularly at the plasma membrane is essential for its phosphatase (PTPase) activity [11-16]. This interaction, not only activates its enzyme function, but also allows its recruitment to target substrates in the cell. Therefore, increased tyrosine phosphorylation in a cell leads to enhanced SHP2 activity. Other events known to activate SHP2 are mutations in the SH2 domains that affect autoinhibition. Some of these mutations result in gain-of-function SHP2 that can promote increased mitogenic and cell survival signaling, leading to human diseases such as Noonan syndrome and hematopoietic malignancies [10, 17, 18]. The disease-causing capacity of activated SHP2 has been experimentally demonstrated where transgenic mice expressing gain-of-function SHP2 mutants develop myeloproliferative disorders [18, 19], supporting the importance of SHP2 in cancer.

In the dephosphorylation reactions of phosphatases, including SHP2, the Asp residue in the so called WPD loop and Cys residue in the active site play essential roles [20]. While the Asp residue acts as a proton donor for the leaving phenolate group of the substrate, the Cys residue executes a nucleophilic attack on the phosphate moiety, leading to hydrolysis of the phosphate moiety. Other residues in the active site of PTPs, also known as the signature motif, such as Arg and Lys residues play substrate binding roles. In addition, Thr and Ser residues in the active site have been shown to play important roles in PTP catalysis [21].

SHP2 is a well-known mediator of mitogenic and cell survival signaling downstream of several signaling pathways [1, 12, 22, 23]. In receptor tyrosine kinase (RTK) signaling, including in epidermal growth factor receptor (EGFR) and human EGFR2 (HER2), SHP2 mediates activation of the Ras-ERK1/2 (extracellular signal regulated kinase 1 and 2) and the PI3K-Akt (phosphatidylinositol 3-kinase—protein kinase B) signaling pathways. One of the mechanisms by which SHP2 mediates Ras activation and consequently of ERK1/2 and PI3K is by blocking the Ras GTPase activating protein (RasGAP), the down regulator of Ras [24, 25]. In EGFR and HER2, SHP2 dephosphorylates phosphorylated Tyr992 (pTyr992) and pTyr1023, respectively, which act as RasGAP binding sites. In Wnt signaling, SHP2 enhances β-catenin signaling by blocking its interaction with α-catenin through dephosphorylation of the latter thereby promoting translocation of the former to the nucleus where it acts as a transcription factor for expression of mitogenic proteins such as c-Myc and cyclin D1 [26]. Similarly, SHP2 promotes Src activation by blocking the translocation of the C-terminal Src kinase (Csk), the Src inhibitor kinase, to the plasma membrane via dephosphorylation of a Csk docking site on PAG (a transmembrane adaptor protein) thereby enhancing Src activation [27]. In all cases, the net effect is increased Tyr kinase signaling to Ras and hence to ERK1/2 and PI3K. It may be this role of SHP2 that allows it to mediate cell transformation induced by oncogenic Tyr kinases [25, 28, 29].

Previous work has shown that SHP2 mediates cell transformation induced by the oncogenic v-Src [29] and the constitutively active form of fibroblast growth factor receptor 3 (K650E-FGFR3) [28]. In addition, SHP2 has been shown to be important for cell transformation induced by the HER2 oncogene [25], and for the growth and transformation phenotype of lung, colon and breast cancer cells [30-32]. These findings suggest that SHP2 plays a cancer promoting role.

The following were the driving forces behind the present invention. First, a large body of literature suggests that SHP2 is a positive mediator of mitogenic and cell survival signaling downstream of the epidermal growth factor receptor (EGFR) [24, 33], HER2, the MET receptor, and several other receptor tyrosine kinase that are dysregulated in breast cancer and many other cancer types [12, 26, 34-38]. Second, recent studies by us and others show that SHP2 is overexpressed in breast cancer with strong association to disease progression and poor clinical outcome [39, 40]. Third, functional studies have shown that SHP2 promotes the transformation phenotype of breast cancer cells and its inhibition suppresses xenograft tumor growth and metastasis [32, 41]. Therefore, inhibition of SHP2 represents a novel therapeutic strategy for the treatment of breast cancer and possibly other cancer characterized by tyrosine kinase activation. To test this possibility, a specific inhibitor of SHP2 must be invented. Based on this real but unmet need, the present invention provides a compound that is an SHP2 inhibitor, derivatives of the compound of this invention, a chemical synthesis scheme for making the compound of this invention, and derivative compounds thereof, and a characterization of the compound of this invention under in vitro and cell culture conditions.

SUMMARY OF THE INVENTION

Figure 1:
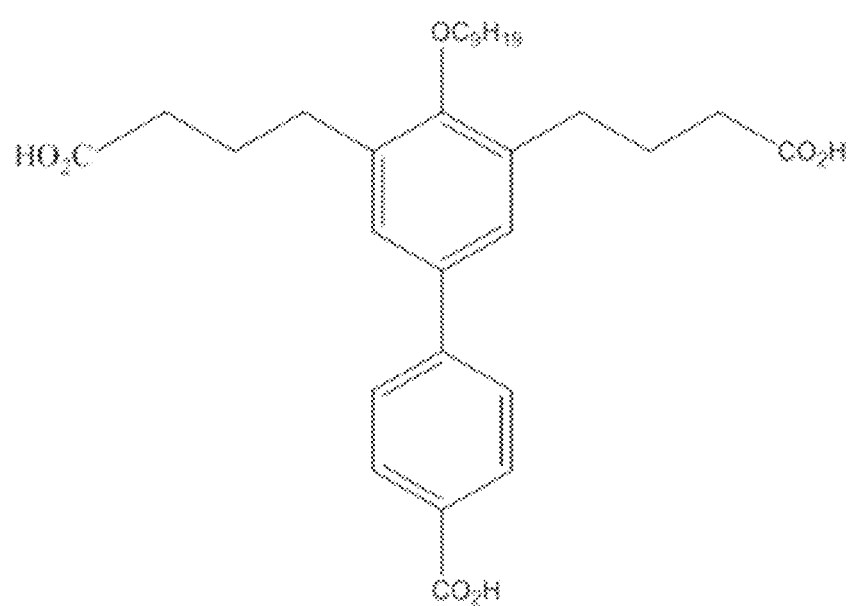
FIG. 1 shows the chemical structure of the synthetic compound 4,4'-(4'-Carboxy)-4-nonyloxy-[1,1'-biphenyl]-3,5-diyl)dibutanoic acid abbreviated as CNBDA.

The present invention refers to inhibition of SHP2 function in vitro and in vivo with a synthetic compound, namely, 4,4'-(4'-Carboxy)-4-nonyloxy-[1,1'-biphenyl]-3,5-diyl) dibutanoic acid (hereinafter "CNBDA"). The mechanism of inhibition is the binding of the specific inhibitor CNBDA to SHP2 particularly to the active site of the phosphotyrosyl phosphatase (PTP) domain.

The present invention further details the specific inhibition of the SHP2 enzyme function in vitro. It also teaches that the anti-SHP2 compound CNBDA inhibits breast cancer cell growth and induces cell death under cell culture conditions.

The present invention also provides compounds that are derivatives of 4,4'-(4'-Carboxy)-4-nonyloxy-[1,1'-biphenyl]-3,5-diyl)dibutanoic acid (CNBDA). For example, but not limited to, this invention provides for the modification of the anti-SHP2 compound CNBDA to create derivatives of the parent compound. These modifications of the parent CNBDA compound to form derivative compounds of CNBDA include a) the changing of one or both of the butyric acid groups of the CNBDA compound to groups having additional carbon atoms in the chain (i.e. longer carbon chains, for example containing greater than 4 carbon atoms) or less carbon atoms in the chains (i.e. shorter carbon chains, for example containing from 1 to three carbon atoms) to form either long-chain organic acids or short-chain organic acids, and may include for example but not limited to from one to 15 carbon atoms, from one to 30 carbon atoms, and from greater than 15 carbon atoms, wherein the carbon atom chains are either saturated, partially saturated, or unsaturated with respect to the carbon to carbon bonding, b) replacement of carboxylic groups with phosphate, sulphate or amide, hydroxyl, aldehyde or halides, and c) replacement of the nonane group with shorter or longer hydrocarbon groups (i.e. hydrocarbon groups have from one to 15 carbon atoms, one to thirty carbon atoms, or greater than 15 carbon atoms).

Another embodiment of this invention provides a compound of the chemical formula:

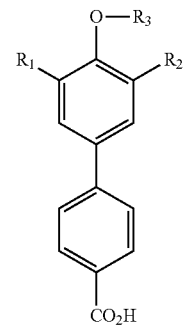

wherein $R_1$ and $R_2$ are the same or different and are independently selected from the group of (a) an organic acid group (carboxylic group) having from 1-30 or more carbon atoms in chain length, wherein the carbon atom chains are either saturated, partially saturated, or unsaturated with respect to the carbon to carbon bonding of the carbon atom chain, and (b) replacement of the carboxylic groups of (a) with a phosphate, a sulphate, an amide, an hydroxyl, an aldehyde, or a halide group, and wherein $R_3$ is an alkane group having from one to thirty or more carbon atoms in chain length.

Another embodiment of this invention provides a pharmaceutical composition comprising a compound of the chemical formula:

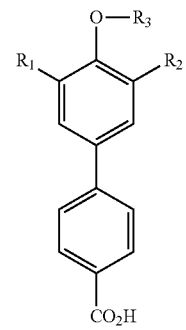

wherein $R_1$ and $R_2$ are the same or different and are independently selected from the group of (a) an organic acid group (carboxylic group) having from 1-30 or more carbon atoms in chain length, wherein the carbon atom chains are either saturated, partially saturated, or unsaturated with respect to the carbon to carbon bonding of the carbon atom chain, and (b) replacement of the carboxylic groups of (a) with a phosphate, a sulphate, an amide, an hydroxyl, an aldehyde, or a halide group, and wherein $R_3$ is an alkane group having from one to thirty or more carbon atoms in chain length, and a pharmaceutically acceptable carrier. The pharmaceutical composition of includes wherein the pharmaceutically acceptable carrier is any known pharmaceutically acceptable carrier and is preferably a pharmaceutical carrier selected from the group consisting of dextrose, water, saline, isotonic saline, and lactose.

Another embodiment of this invention provides a pharmaceutical composition comprising a compound that is 4,4'-(4'-Carboxy)-4-nonyloxy-[1,1'-biphenyl]-3,5-diyl) dibutanoic acid (abbreviated "CNBDA") having the following chemical structure:

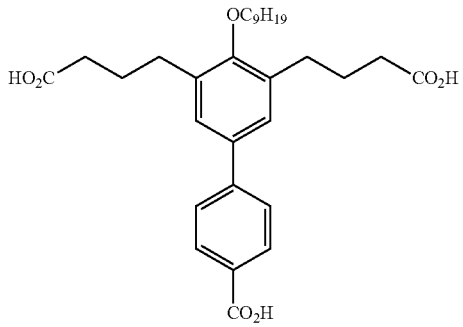

wherein said chemical structure has a biphenyl backbone having a lower positioned phenyl group that is attached to an upper positioned phenyl group, wherein a carboxylate group is attached to said lower phenyl group, and two butyric acid groups each attached at different positions to said upper phenyl group, and a nonyloxy group attached to said upper phenyl group at a position between each of said butyric acid groups, and a pharmaceutically acceptable carrier. In a preferred embodiment of this invention, the pharmaceutical composition as described herein, includes a derivative of CNBNA wherein said derivative compound has one or more of the following substitutions (a) replacement of one or both of said butyric acid groups of the CNBDA compound with an organic acid group (carboxylic group) having from 1-3 carbon atoms in chain length, or having from 5 to 30, or more carbon atoms in chain length, wherein the carbon atom chains are either saturated, partially saturated, or unsaturated with respect to the carbon to carbon bonding of said carbon atom chain, (b) replacement of said carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty, or more carbon atoms in chain length.

DETAILED DESCRIPTION OF THE INVENTION

The present invention provides the compound 4,4'-(4'-Carboxy)-4-nonyloxy-[1,1'-biphenyl]-3,5-diyl)dibutanoic acid (CNBDA), and the chemical synthesis of CNBDA, and the use of CNBDA for inhibition of SHP2 function in vitro and in vivo. The present invention discloses use of CNBDA for inhibition of SHP2 function in research and diagnostic procedures and its use in the treatment of cancer (i.e. CNBDA as an anti-cancer agent).

As used herein the term "anti-SHP2 compound" refers to the synthetic compound 4,4'-(4'-Carboxy)-4-nonyloxy-[1,1'-biphenyl]-3,5-diyl)dibutanoic acid, abbreviated as CNBDA and its derivatives. Derivatives mean a) longer- or shorter-chain organic acids replacing butyric acid functional groups in CNBDA, for example but not limited to replacing of one or both of the butyric acid groups of the CNBDA compound to groups having additional carbon atoms in the chain (i.e. longer carbon chains, for example containing greater than 4 carbon atoms) or less carbon atoms in the chains (i.e. shorter carbon chains, for example containing from 1 to three carbon atoms) to form either long-chain organic acids or short-chain organic acids, and may include for example but not limited to from one to 15 carbon atoms, from one to 30 carbon atoms, and from greater than 15 carbon atoms, wherein the carbon atom chains are either saturated, partial saturation, or unsaturated with respect to the carbon to carbon bonding, b) phosphate, sulfate, amide, hydroxyl, aldehyde or halides groups replacing carboxylic groups in CNBDA, and c) shorter or longer hydrocarbon groups replacing the nonane group in CNBDA, such as for example but not limited to hydrocarbon groups having from one to 15 carbon atoms, one to thirty carbon atoms, or greater than 15 carbon atoms. The length of the carbon chains may vary and for example includes from one to 15 or more carbon atoms. The bonds between the carbon atoms may be saturated, partially saturated, or unsaturated.

As used herein, the term "effective amount" refers to that amount of a substance or compound that is required to bring about a desired effect. For example, an effective amount of a compound to treat a disease, such as for example cancer, is that amount of the compound required to treat cancer.

As used herein, the term "patient" refers to any member of the animal family and includes human beings.

The rational design of CNBDA was based on knowledge gained from previous studies by the inventor that the biological substrates of the SHP2 PTP activity possess acidic residues N-terminal to the phosphotyrosyl substrate [25] and that isolated peptides with such properties can act as specific SHP2 inhibitors as described in the issued patent to the inventor (U.S. Pat. No. 7,547,760 B2). The chemical structure of the compound CNBDA of the present invention is shown below.

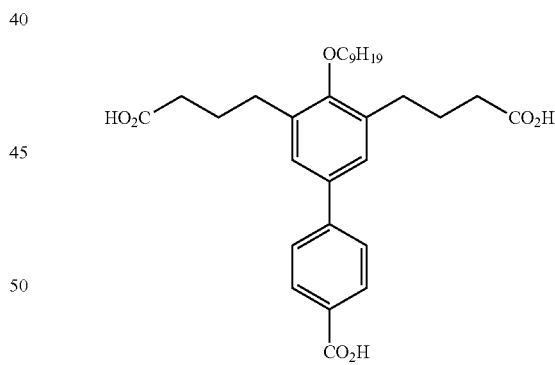

FIG. 1 also shows the structure CNBDA. The chemical structure of CNBDA contains a biphenyl backbone with carboxylate group to partially mimic phosphotyrosine, two butyric acid groups to mimic acidic residues in protein substrates of SHP2, and a nonyloxy group (a 9-carbon alkane with ether bond) to allow cell penetration.

A) Detailed Protocol for Synthesis of CNBDA

1. Methyl 4'-hydroxy-[1,1'-biphenyl]-4-carboxylate (2): Concentrated sulfuric acid (~0.5 mL) was added to a suspension of 4'-hydroxy-[1,1'-biphenyl]-4-carboxylic acid (5.00 g, 23.36 mmol, 1.0 equiv)in methanol (100 mL) and the mixture refluxed with a yellow-brown solution developing. After ~1.5 hr (hour), a suspension began forming.

After 15 hr of reflux, the suspension was cooled to room temperature, then in an ice-bath. The solid was filtered, washed with cold methanol (2×25 mL) and dried to give compound 2 (4.84 g) as a tan solid.

2. Methyl 3',5'-dibromo-4'-hydroxy-[1,1'biphenyl]-4-carboxylate (3): Bromine (1.45 mL, 28.46 mmol, 2.2 equiv) was added dropwise to a suspension of compound 2 (2.95 g, 12.94 mmol, 1.0 equiv) in acetic acid (75 mL). The reaction temperature slowly increased from 17 to 22° C. and the solids dissolved to give an orange-brown solution. The mixture was stirred overnight at room temperature. The resulting yellow-orange suspension was slowly diluted with cold water (300 mL) and the suspension stirred 0.5 hr. The solid was filtered, washed with water (3×100 mL) and the solid dried on the filter for 0.5 hr. The solid was dissolved in ethyl acetate (250 mL) and the solution was washed with a mixture of saturated sodium bicarbonate solution (75 mL) and saturated sodium thiosulfate solution (75 mL) followed by saturated brine (100 mL). The organic solution was dried over sodium sulfate, filtered, and the filtrate concentrated to near dryness. The solid was triturated with heptanes (50 mL), filtered, washed with heptanes and dried to give compound 3 (3.94 g) as a tan solid. Additional compound 3 (0.82 g) was obtained by concentration of the heptanes filtrate under reduced pressure.

3. Methyl 3',5'-dibromo-4'-methoxy-[1,1'biphenyl]-4-carboxylate (4): A mixture of compound 3 (4.76 g, 12.33 mmol, 1.0 equiv). dimethyl sulfate (1.86 g, 1.40 mL, 14.79 mmol, 1.2 equiv) and potassium carbonate (2.55 g, 18.50 mmol, 1.5 equiv) in acetone (125 mL) was refluxed for 6 hr. The suspension was cooled to room temperature, filtered, washing the solids with acetone (50 mL). The filtrate was concentrated under reduced pressure to give a yellow viscous oil. The viscous oil was partitioned between a 2:1 mixture of ethyl acetate/heptanes (300 mL) and water (100 mL)—slow phase separation. The organic phase was washed with water (100 mL), saturated brine (100 mL), dried over sodium sulfate, filtered, and the filtrate concentrated under reduced pressure to give a yellow-brown, gummy foam. The residue was purified on an AnaLogix automated chromatography system (SF25-60 g column, dryloaded) eluting with a gradient of 5 to 20% ethyl acetate in heptanes to give compound 4 (1.29 g) as a white solid.

4. Diethyl 4,4'-(4'-methoxycarbonyl)-4-methoxy-[1,1'-biphenyl]-3,5-diyl)-dibutanoate and diethyl 4,4'-(4'-ethoxycarbonyl)-4-methoxy-[1,1'-biphenyl]-3,5-diyl)dibutanoate (5): A suspension of compound 4 (1.29 g, 3.23 mmol, 1.0 equiv), and [1,1'-bis(diphenylphosphino)ferrocene)dichloropalladium(II) complex with dichloromethane (0.24 g, 10 mol %) in tetrahydrofuran was degassed with a stream of nitrogen for 5 min. A 0.5M solution of 4-ethoxy-4-oxobutylzinc bromide in tetrahydrofuran (26 mL, 13 mmol, 4.02 equiv) was added via syringe. The resulting brown solution was refluxed for 18 hr. The mixture was cooled to room temperature and quenched with saturated ammonium chloride (20 mL). The biphasic mixture was diluted with water (20 mL) and extracted with a 1:1 mixture of ethyl acetate and heptanes. The organic phase was washed with water (50 mL), saturated brine (2×50 mL), dried over sodium sulfate, filtered and the filtrate concentrated under reduced pressure. The resulting red-brown oil was purified on an AnaLogix automated chromatography system (SF15-24 g column, dryloaded) eluting with a gradient of 0 to 30% ethyl acetate in heptanes. Fractions containing the higher $R_f$ closely running components were concentrated to give compound A (0.4 g, not shown) as a colorless oil. Fractions containing the lower $R_f$ closely running components were concentrated to give compound 5 (0.89 g) as a yellow-brown oil. Note 1: Compound A arises by insitu reduction of the initially formed mono-Negishi coupled product. Note 2: Compound 5 (mixture of triethyl and diethyl, monomethyl esters) was obtained due to partial transesterification that occurred during the Negishi coupling reaction.

5. Diethyl 4,4'-(4'-ethoxycarbonyl)-4-methoxy-[1,1'-biphenyl]-3,5-diyl)dibutanoate (6): Concentrated sulfuric acid (4 drops) was added to a solution of compound 5 (0.89 g) in ethanol (40 mL) and the mixture heated at reflux for 10 hr. The solution was cooled to room temperature and stirred overnight at room temperature. The mixture was concentrated under reduced pressure to remove ethanol. The residual oil was dissolved in ethyl acetate and the solution washed with saturated sodium bicarbonate (25 mL), saturated brine (25 mL), dried over sodium sulfate, filtered and the filtrate concentrated under reduced pressure. The crude brown oil was purified on an AnaLogix automated chromatography system (SF15-24 g column, dryloaded) eluting with a gradient of 0 to 25% ethyl acetate in heptanes to give compound 6 (64 g) as a pale yellow oil.

6. 4,4'-(4'Carboxy)-4-hydroxy-[1,1'-biphenyl]-3,5-diyl)dibutanoic acid, mixture of methyl and ethyl esters (7): A solution of compound 6 (1.10 g, ~2.27 mmol, 1.0 equiv) in dichloromethane (40 mL) was cooled in an ice-bath and 1.0M boron tribromide in dichloromethane (7.0 mL, 7 mmol, 3.08 equiv) was added drop-wise. The mixture was stirred in the ice-bath for 4.5 hr, then quenched by the slow, dropwise addition of methanol. The mixture was allowed to warm to room temperature and stirred overnight. The mixture was concentrated under reduced pressure and the residual yellow-brown oil dissolved in ethyl acetate (75 mL). The solution was washed sequentially with water (2×50 mL), saturated sodium bicarbonate (50 mL) and saturated brine (50 mL). The organic phase was dried over sodium sulfate, filtered and the filtrate concentrated under reduced pressure to give crude compound 7 (1.0 g) as a yellow-brown oil. Crude compound 7 was used subsequently.

7. 4,4'-(4'-Carboxy)-4-nonyloxy-[1,1'-biphenyl]-3,5-diyl)dibutanoic acid, mixture of methyl and ethyl esters (8): A mixture of potassium carbonate (0.47 g, 3.41 mmol, ~1.5 equiv), crude compound 7 (1.00 g, ~2.27 mmol, 1.0 equiv) and acetonitrile (25 mL) was stirred 5 min. 1-Bromononane (0.59 g, 0.54 mL, 2.84 mmol, ~1.25 equiv) was added and the mixture refluxed for 5.5 hr. After stirring overnight at room temperature, the suspension was filtered and the solids washed with ethyl acetate (25 mL). The filtrate was concentrated under reduced pressure. The residual oil was partitioned between ethyl acetate (75 mL) and water (25 mL)—slow phase separation. The organic phase was washed with saturated brine (25 mL), dried over sodium sulfate, filtered and the filtrate concentrated to give a light brown oil. The crude product was purified on an AnaLogix automated chromatography system (SF15-24 g column, dryloaded) eluting with a gradient of 0 to 25% ethyl acetate in heptanes to give compound 8 (0.97 g) as a colorless oil.

8. 4,4'-(4'-Carboxy)-4-nonyloxy-[1,1'-biphenyl]-3,5-diyl)dibutanoic acid (WVU1000c): A solution of lithium hydroxide monohydrate (1.02 g, 25 mmol, 14.7 equiv) in water (25 mL) was added to a solution of compound 8 (0.97 g, ~1.70 mmol, 1.0 equiv) in tetrahydrofuran (25 mL). On addition, the resulting biphasic mixture warmed slightly. The mixture was stirred at room temperature for 19.5 hr., when TLC (50% ethyl acetate/heptanes) and LCMS showed the reaction was complete. The mixture was concentrated under reduced pressure to remove tetrahydrofuran. The residual aqueous solution was cooled in an ice-bath and made acidic (pH 1) with 1N hydrochloric acid to give a fine white precipitate. The aqueous suspension was extracted with 10:1 mixture of ethyl acetate and tetrahydrofuran (275 mL). [Note: The solid was only partially soluble in ethyl acetate.] The organic phase was washed with saturated brine (100 mL), dried over sodium sulfate, filtered and the filtrate concentrated under reduced pressure to give a white solid. The solid was dried overnight in a vacuum oven at 50° C. to give CNBDA (776 mg) as a white solid.

NMR (DMSO-$d_6$): δ 0.88 (t, 3H), 1.28 (m, 10H), 1.48 (m, 2H), 1.75 (m, 2H), 1.84 (m, 4H), 2.27 (t, 4H), 2.65 (t, 4H), 3.75 (t, 2H), 7.41 (s, 2H), 7.68 (d, 2H), 8.00 (d, 2H), 12.25 (bs, 3H).

Figure 2:
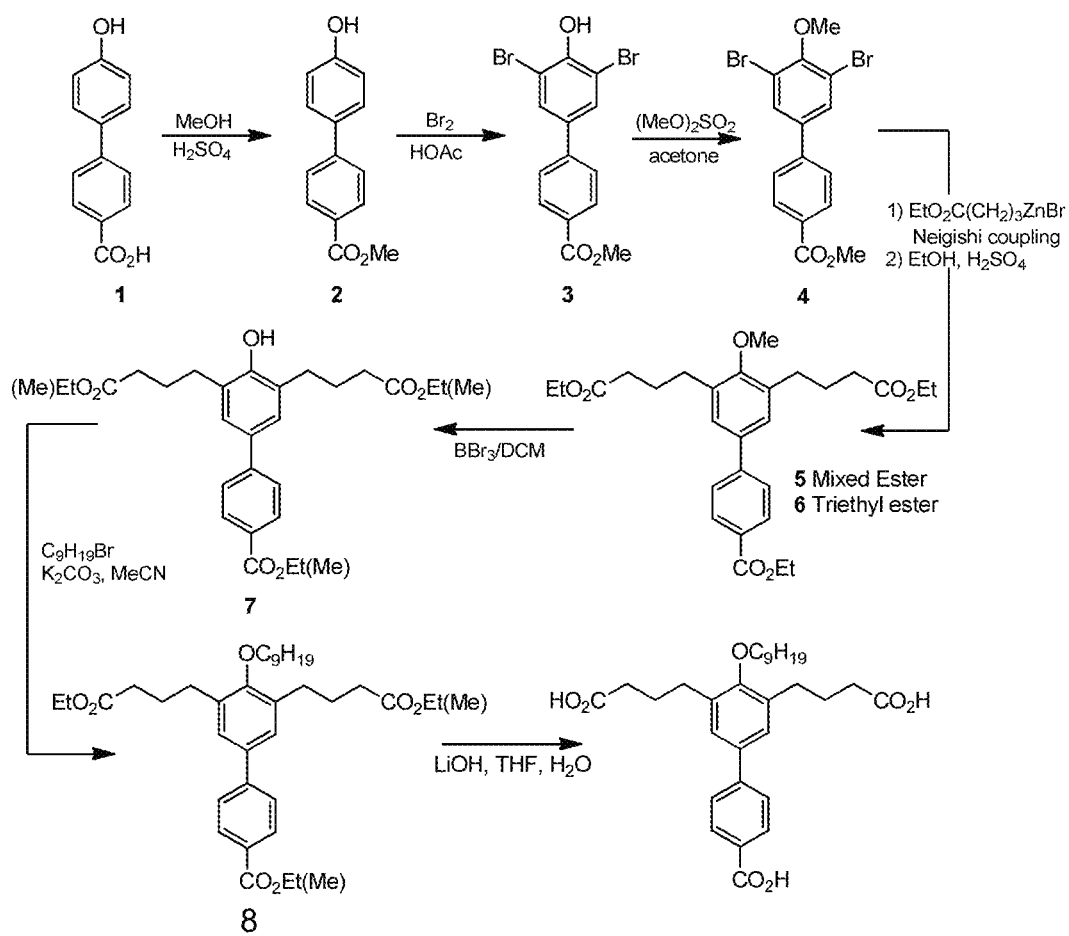
FIG. 2 shows the scheme for the synthesis of 4,4'-(4'-Carboxy)-4-nonyloxy-[1,1'-biphenyl]-3,5-diyl) dibutanoic acid.

FIG. 2 shows the synthesis scheme for making CNBDA. Those persons skilled in the art are capable of making the derivatives of CNBDA as described herein (see chemical formula II, below) since the reaction(s) needed to accomplish the replacement group(s) are straightforward and well known. For example, in FIG. 2 showing the detailed protocol for the synthesis of CNBDA, step 4 can be modified by those persons skilled in the art to provide derivatives at the $R_1$ and $R_2$ locations of formula II (shown below). On the other hand, step 7 of FIG. 2 can be modified by those persons skilled in the art to provide derivatives of CNBDA at the $R_3$ location of formula II (shown below).

B) Functional Characterization of CNBDA

C-1: Predicting the Binding Modalities of CNBDA to SHP2 and SHP1 Active Sites

Figure 3:
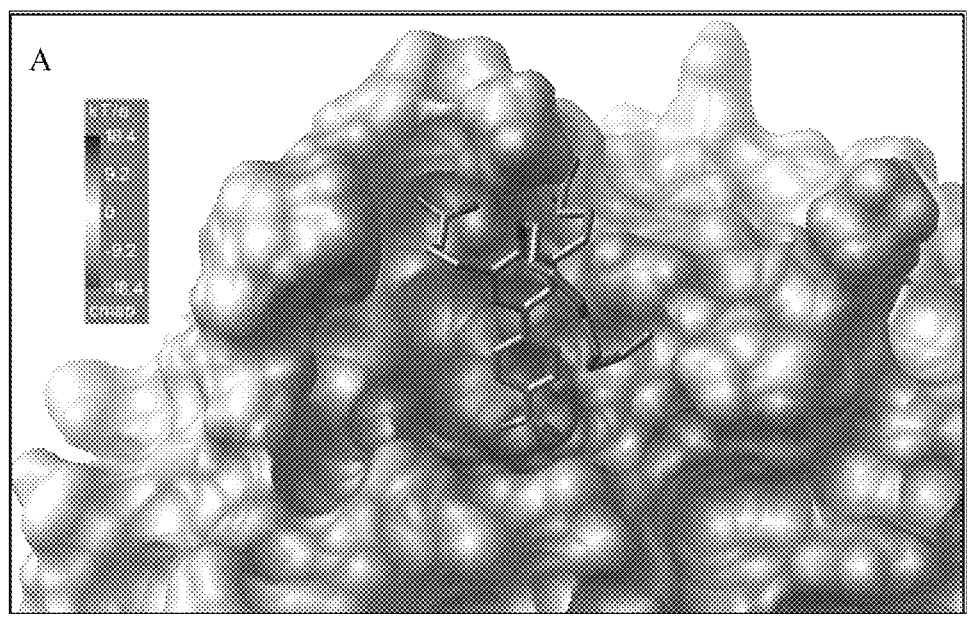
FIG. 3 shows docking studies of CNBDA to the active site of SHP2.
Figure 4:
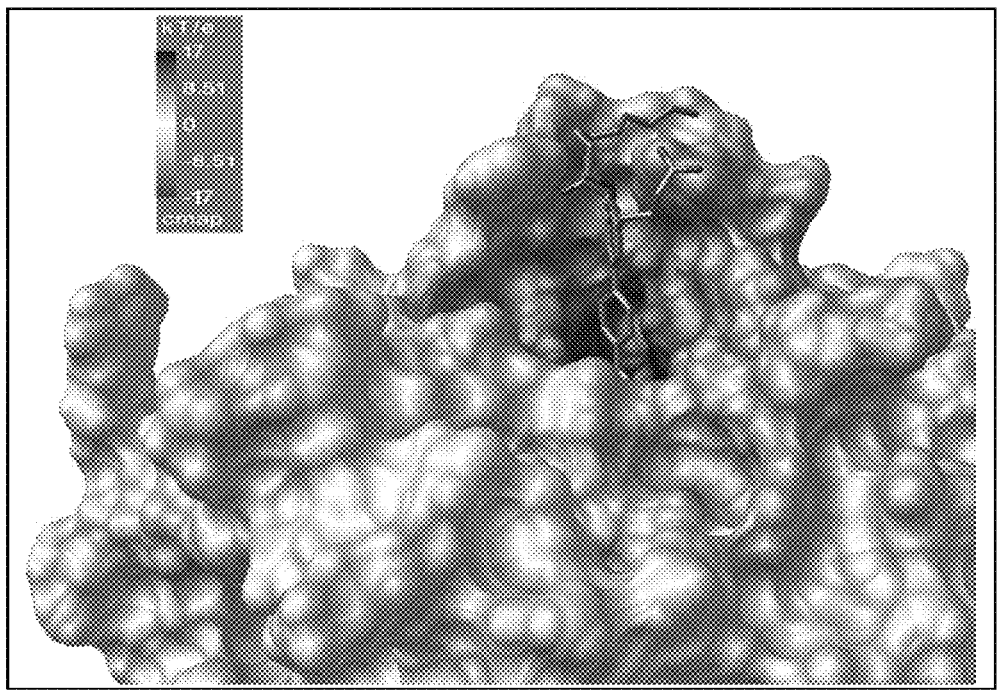
FIG. 4 shows docking studies of CNBDA to the active site of SHP1.

Initially, in silico binding studies were performed to predict the binding properties of CNBDA to the active site of the SHP2 and SHP1 PTP domains. CNBDA was docked into the active sites of SHP2 (PDB:2SHP) [2] (FIG. 3) and SHP1 (PDB:1GWZ) [42, 43] (FIG. 4) using the genetic algorithm in Autodock4 [44]. The compound was predicted to bind SHP2 with an affinity of 1.48 µM while it was predicted to bind SHP1 with 17.42 µM affinity, suggesting that CNBDA has more than 10-fold affinity for SHP2 than SHP1. In the SHP2 active site, the carboxylate groups provided by butanoic acids of CNBDA make electrostatic interaction with lysine 364 and lysine 366 while the biphenyl bearing the carboxyl group buries itself in the catalytic cleft in a fashion similar to the phosphotyrosine substrate (FIG. 3). Arginine 358 of SHP1 that corresponds to lysine 366 of SHP2 was also found to interact with the negatively-charged carboxylates of CNBDA, but steric repulsion prevented the necessary geometry to optimize the electrostatic interactions (FIG. 4). Similarly, lysine 356 of SHP1 is in position to a CNBDA carboxylate group but could not make meaningful interaction. Overall, analysis of the energies of interaction revealed that the geometries of the SHP2 and SHP1 active sites created different binding modalities for CNBDA. SHP1 possesses an arginine residue at position 358, which corresponds to SHP2's lysine 364. The increased size of the arginine side chain in SHP1 appears to engender steric hindrance to binding. This results in poor geometry for electrostatic interactions. In total, the predicted contribution of electrostatic interactions played in the predicted binding was −5.83 and −3.52 kcal/mol for CNBDA binding to SHP2 and SHP1, respectively. This difference in electrostatic interaction stabilization was the largest contributor to the different intermolecular energies.

FIG. 3 shows the interaction of CNBDA with the PTP domain of SHP2. Filled electron map of the SHP2 PTP domain and stick diagram of CNBDA are shown. The inset depicts scale of electrostatic charge on the surface of the active site.

FIG. 4 shows the interaction of CNBDA with the PTP domain of SHP1. Filled electron map of the SHP1 PTP domain and stick diagram of CNBDA are shown. The inset depicts scale of electrostatic charge on the surface of the active site.

C-2: Testing Effect of CNBDA on the Phosphatase Activities of SHP2 and SHP1

The effect of CNBD on the SHP2 phosphatase activity was tested using the artificial substrate DiFMUP (6,8-difluoro-4-methylumbelliferyl) at a concentration of 20 µM, which is commonly used in phosphatase assays [45, 46]. CNBDA concentrations of 1.94 mM, 194 µM, 97 µM, 48.5 µM, 24.25 µM, 19.4 µM, 12.9 µM, and 1.94 µM in water were used in the analysis. The PTP domains of SHP2 and SHP1 fused to glutathione-S-transferase (GST-PTPs) were expressed in E. coli using a standard protein expression protocol and purified on glutathione sepharose beads as recommended by the manufacturer (Pharmacia), and quantified by measuring absorbance at 280 nm and comparison with BSA standards. Reactions were performed at 30° C. in 100 µl volume of PTPase buffer containing 25 mM Tris-HCl pH7.0, 50 mM NaCl, 2 mM EDTA and 10 mM dithiothreitol (DTT). Change in absorbance (production of DiFMU, dephosphorylated form of DiFMUP) was followed in a plate-reading visible spectrophotometer at 450 nm. Final result was an IC50 of 11.97 uM for SHP2 and 122.4 uM for SHP1. Altogether, this demonstrates that CNBDA is a competitive SHP2 inhibitor that is 10-fold selective for SHP2 over SHP1.

Figure 5A:
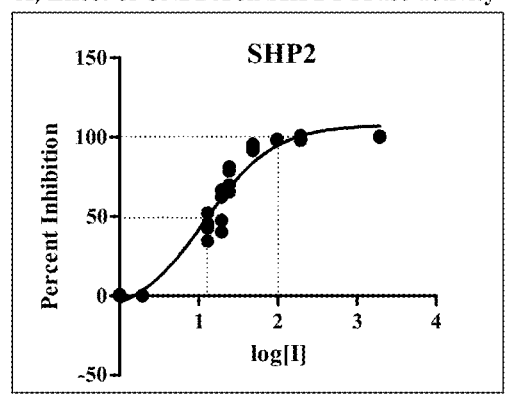
FIG. 5A shows the effect of CNBDA on the phosphatase activity of SHP2.
Figure 5B:
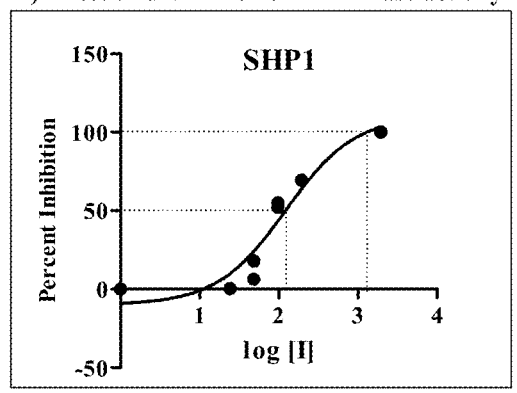
FIG. 5B shows the effect of CNBDA on the phosphatase activity of SHP1.

FIG. 5A shows the effect of CNBDA on the phosphatase activity of SHP2, and FIG. 5B shows the effect of CNBDA on the phosphatase activity of SHP1.

Figure 6A:
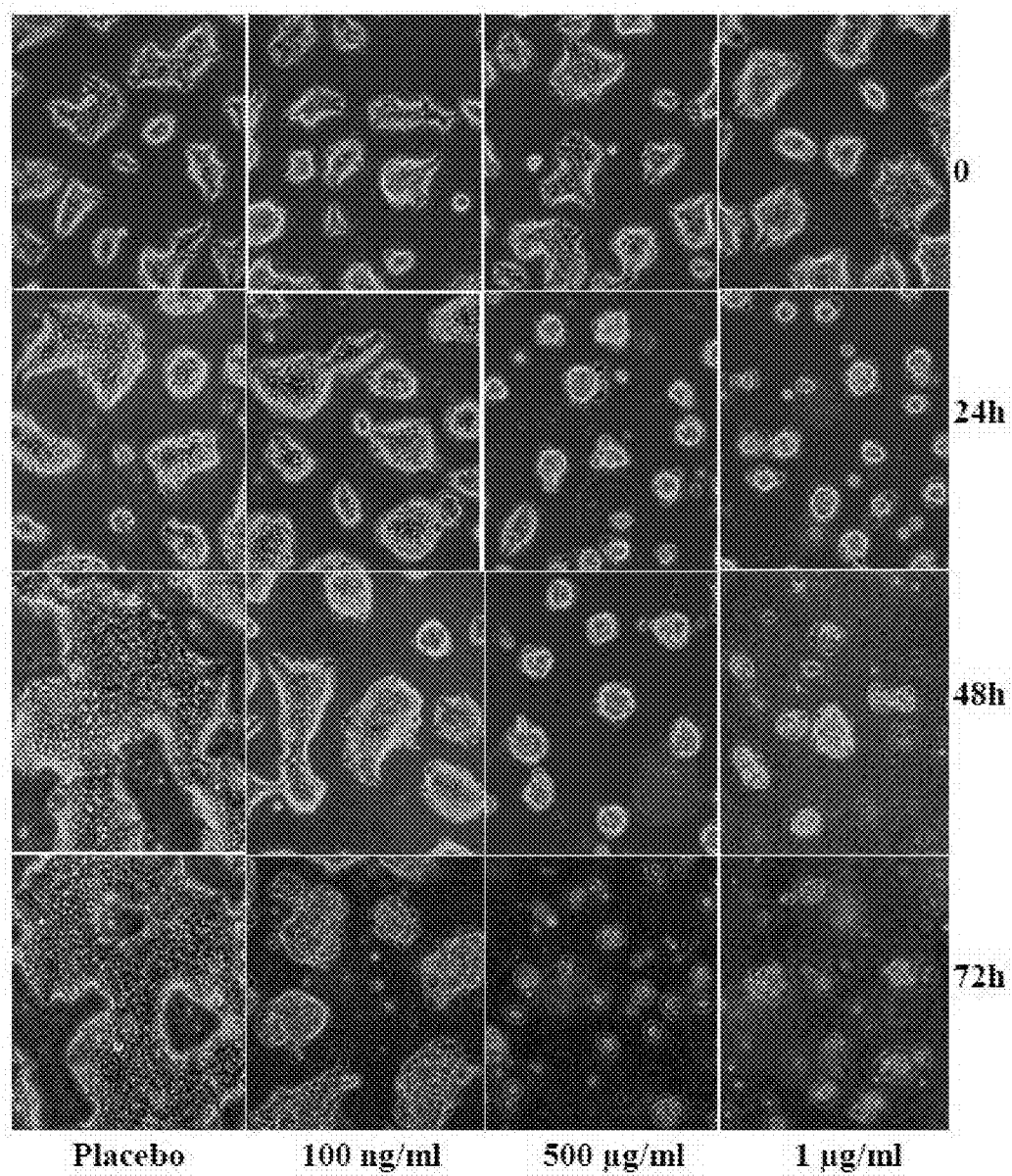
FIG. 6A shows the effect of CNBDA on the growth of HER2-positive BT474 breast cancer cell lines.
Figure 6B:
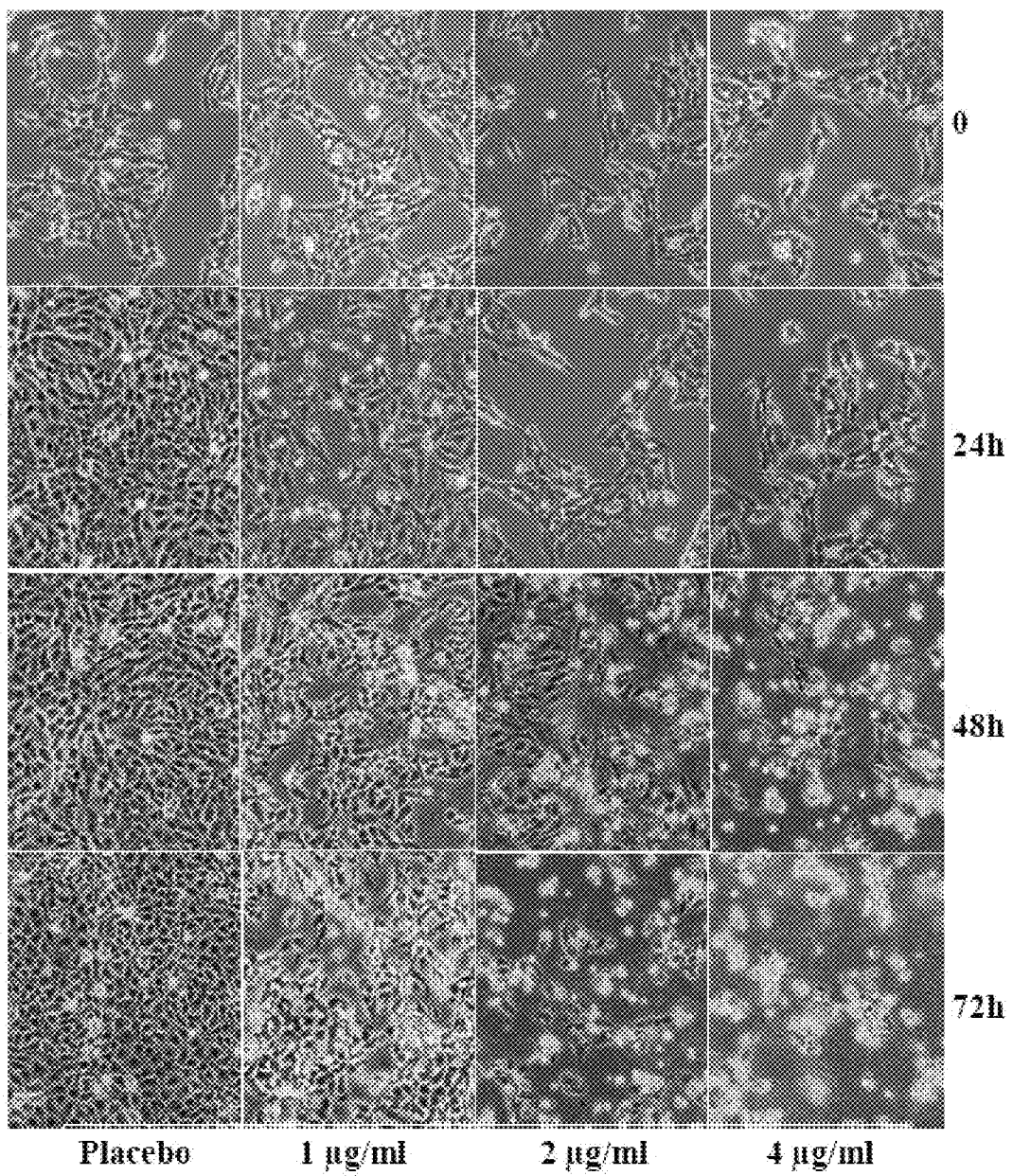
FIG. 6B shows the effect of CNBDA on the growth of EGFR-amplified MDA-MB468 basal-like breast cancer cell line.
Figure 6C:
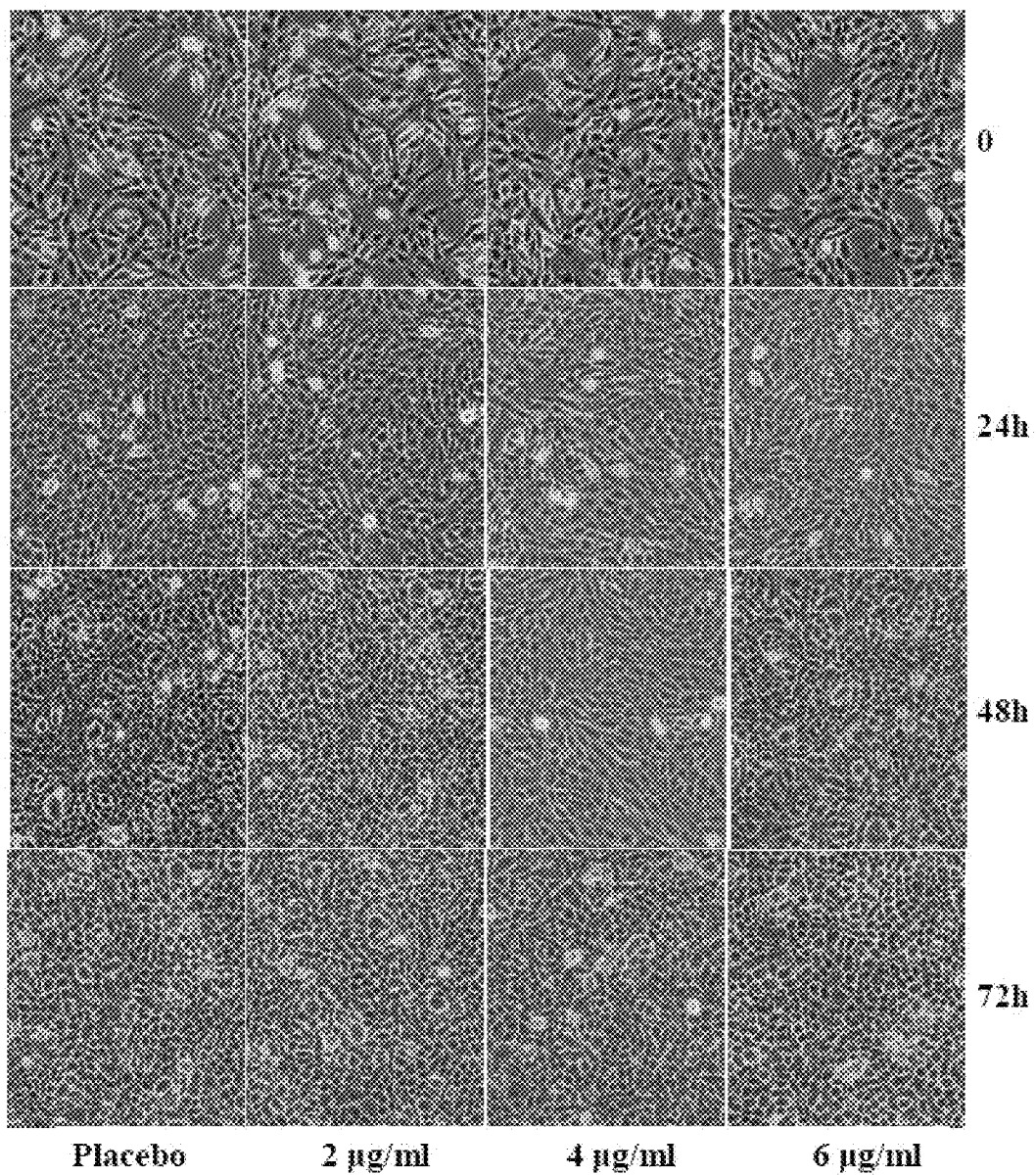
FIG. 6C shows the effect of CNBDA on the growth of the non-tumorigenic MCF-10A breast epithelial cells.

C-3: Testing the Effect of CNBDA on the Growth and Transformation of Breast Cancer Cells Recent reports by us and others show that SHP2 is overexpressed in breast cancer [39, 40] and its inhibition reverses breast cancer cell transformation [25, 30, 32, 46]. Therefore, the anti-cancer activity of CNBDA was tested in breast cancer cells under 2-dimensional (culture plates), soft agar, and suspension cultures. Because SHP2 is an essential downstream mediator of receptor tyrosine kinase (RTK) signaling, including HER2 and HER1 [24, 25], breast cancer cells that harbor dysregulated RTK and SHP2 signaling [40] were chosen for testing the effect of CNDBA. Accordingly, the BT474 cell line that overexpress the human epidermal growth factor receptor 2 (HER2) and the MDA-MB468 cell line that overexpress HER1 (also known as EGFR) were used. The non-transformed MCF-10A breast epithelial cells were used as a "normal" control in these studies. The BT474 cells were grown in RPMI 1640, while the MDA-MB468 cells were grown in Dulbecco's Modified Eagle's Medium (DMEM), both supplemented with 10% fetal calf serum. On the other hand, the MCF-10A cells were grown in DMEM supplemented with 10 mg/ml recombinant human insulin, 20 ng/ml EGF (PeproTech), 0.5 mg/ml hydrocortisone, 100 ng/ml cholera toxin (Sigma) and 5% horse serum, as described previously [47]. All cells were grown in a 37° C. incubator supplied with 5% CO2. In the 2D culture studies, cells were treated with vehicle alone (PBS: phosphate buffered saline) or three different concentration of CNBDA. When the density of cells reached approximately 30%, each plate was treated with vehicle alone (placebo) or the indicated concentrations of CNBDA. In the HER2-positive BT474 breast cancer cell line, CNBDA suppressed cell growth at the lowest concentration used (100 ng/ml) as determined by absence of gradual increase in cell density (FIG. 6A). But, at the 72 hour time point, it was possible to see signs of cell death as evidenced by shrinkage in in the extended patchy growth property of these cells. At 500 ng/ml and higher concentrations, CNBDA induced cell death within 24 hours which became more evident gradually. Similar effects of CNBDA were observed in the MDA-MB468 basal-like breast cancer cell line that overexpress HER1 (FIG. 6B), but at double the concentration that showed effect in the HER2-positive BT474 cells. On the other hand, CNBDA showed very little effect on the growth of the normal control MCF-10A cells (FIG. 6C). These findings show that CNBDA acts primarily on breast cancer cells that rely on dysregulated receptor tyrosine kinase and SHP2 signaling.

Next, the efficacy of CNBDA was evaluated by the soft agar assay, a technique commonly used to determine ability of cells to grow in an anchorage-independent manner [25, 32], one of the hall marks of a cancer cell. The HER2-positive BT474 and the HER1-positive MDA-MB468 cells were seeded in soft agar, treated with placebo or CNBDA at variable concentrations, cultured for 10 days, and their ability to form colonies was monitored by observation under a microscope. The results showed suppression of colony formation by CNBDA in a concentration dependent manner. While the placebo-treated BT474 and MDA-MB468 cells formed larger and numerous colonies in 10 days, the CNBDA-treated counterparts formed smaller and fewer ones (FIG. 6B). In addition, the concentration of CNBDA that abolished colony formation in soft agar was at least 4-fold lower than the amount that caused cell death in 2D cultures in both cell lines (compare FIGS. 6A and 6B). These results show that inhibition of SHP2 with CNBDA suppresses anchorage-independent growth in breast cancer cells.

Finally, the effect of CNBDA on the above mentioned breast cancer cells (BT474 and MDA-MB468) was evaluated by the mammosphere formation assay in which cells with stem-like properties (including cancer stem cells) only can survive and form these structures [48, 49]. Briefly, cells were cultured in ultra-low adherence plates (1×106 cells per 6 cm plate) in a medium containing serum-free DMEM, 1 µg/ml hydrocortisone, 10 µg/ml insulin, 10 ng/ml EGF, 10 ng/ml FGF, 5 ng/ml heparin, and B27 (Invitrogen). After 10 days of culture, primary mammosphere formation was determined by observation under a microscope at which time pictures of mammospheres was taken at 4×objective. Next, the primary mammospheres were collected by centrifugation at 1000 rpm, dissociated to single cells by trypsination and pipetting, and re-cultured under same conditions to observe effect of SHP2 silencing on secondary mammosphere-forming capacity. Pictures of secondary cultures also were taken after 10 days at 4×objective. Comparison of the 4×objective pictures showed an increase in mammosphere-forming capacity in the placebo cells on passaging from primary to secondary cultures and an exhaustion in the CNBDA-treated counterparts (FIG. 6F). Similar to the anchorage-independent growth studies, the concentration of CNBDA that led to exhaustion of mammosphere formation was 4-5 fold lower than the amount needed for cell killing in the 2D cultures. These findings show that CNBDA abolishes cancer stem cell properties of breast cancer cells.

In conclusion, the cell culture studies demonstrate that inhibition of SHP2 with CNBDA suppresses cell growth and reveres transformation, indicating its efficacy as an anti-cancer agent. In addition, the cell culture studies show that the efficacy of CNBDA is higher in cell cultures that better mimic the in vivo conditions—colony formation in soft agar and mammosphere formation in suspension cultures.

FIG. 6A shows the effect of CNBDA on the growth of HER2-positive BT474 cell line at zero hours (h), 24h, 48h, and 72h at CNBDA concentrations of 100 ng/ml, 500 m/ml, and 1 µg/ml, respectively, and as compared to placebo. As shown in FIG. 6A, CNBDA blocks cell growth and induces cell death in a concentration-dependent manner. At the lowest concentration used, CNBDA was able to block cell growth and induction of cell death was apparent only after 48 hours. CNBDA was able to induce cell death within 24 hours at a concentration of 500 ng/ml and greater.

FIG. 6B shows the effect of CNBDA on the growth of the EGFR-amplified MDA-MB468 basal-like breast cancer cell line. As shown in FIG. 6B, CNBDA blocks cell growth and gradually induces cell death. The concentration of CNBDA was determined based on pilot studies that showed 1 µg/ml as the minimum needed to induce cell death in the MDA-MB468 cells after 48 hours. Higher concentrations can induce cell death in relatively shorter treatment times.

FIG. 6C shows the effect of CNBDA on MCF-10A cells, non-transformed, i.e. non-tumorigenic MCF-10A breast epithelial cells. As shown in FIG. 6C, CNBDA did not cause a significant decrease in cell growth or induce cell death even at the higher concentration used, 6 µg/ml.

Figure 6D:
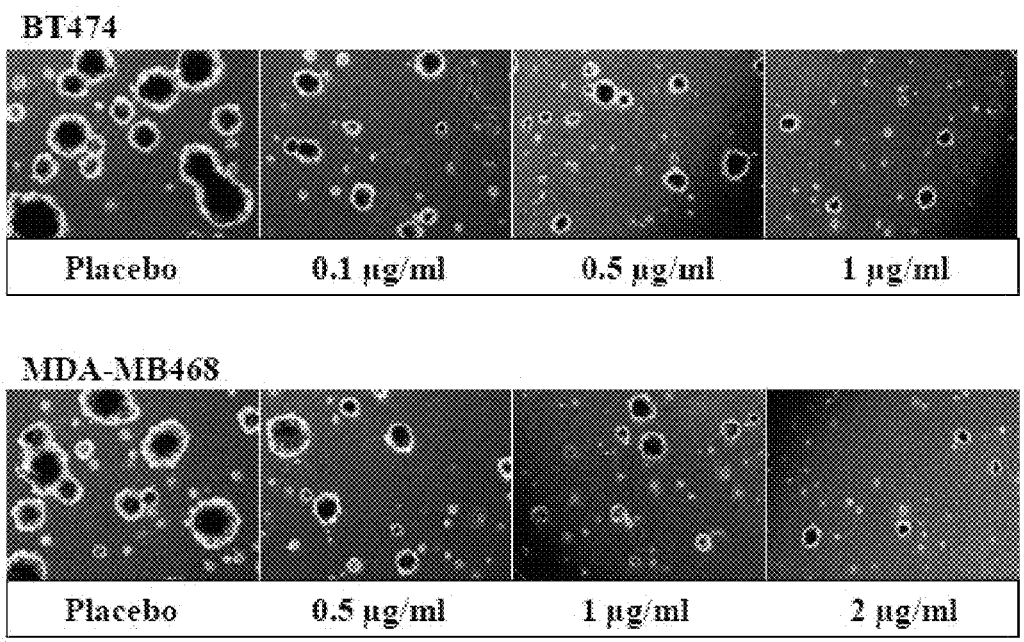
FIG. 6D shows the effect of CNBDA on anchorage-independent growth in soft agar.

FIG. 6D shows the effect of CNBDA on anchorage-independent growth in soft agar. As shown in FIG. 6D, CNBDA suppressed colony formation in soft agar by both the BT474 and the MDA-MB468 cells in a concentration dependent manner. Note than the number and size of colonies decreases as the concentration of CNBDA increases. Also note that the concentration of CNBDA that abolished colony formation in the HER2-positive BT474 breast cancer cell line is 2-fold lower than the amount used in the MDA-MB468 cells.

Figure 6E:
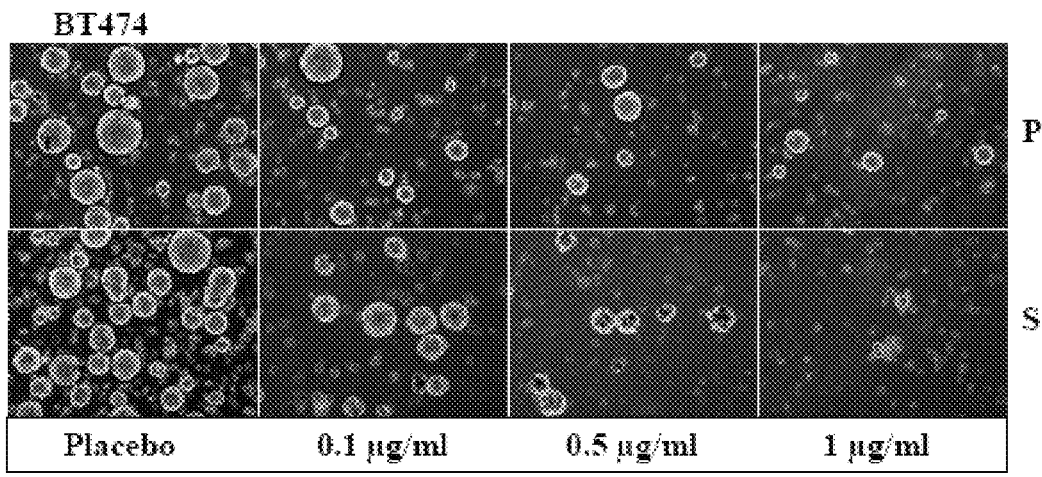
FIG. 6E shows the effect of CNBDA on mammosphere formation in suspension cultures.
Figure 6E:
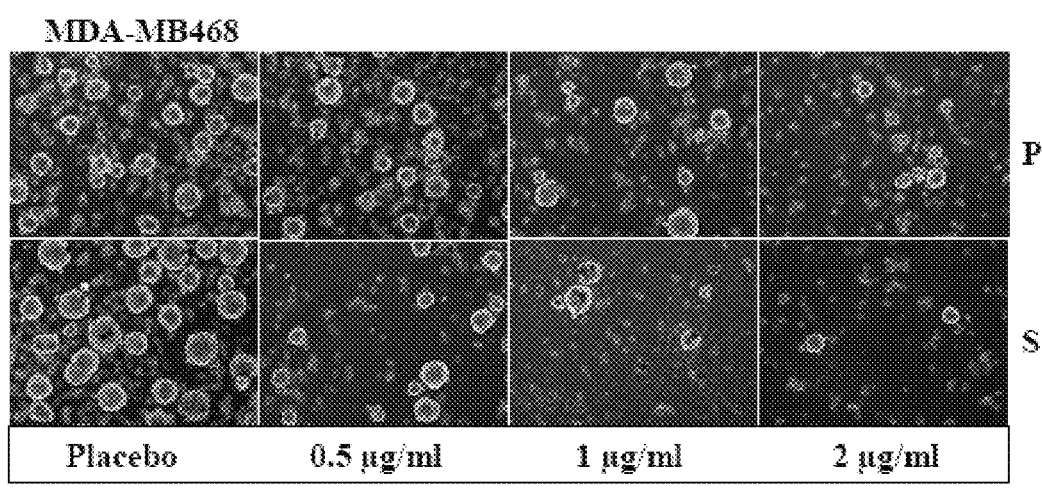

FIG. 6E shows the effect of CNBDA on mammosphere formation in suspension cultires. As shown in FIG. 6E, CNBDA suppressed mammosphere formation by both the BT474 and the MDA-MB468 breast cancer cells in a concentration dependent manner. Note than the number and size of mammospheres decreases as the concentration of CNBDA increases. Also note that the concentration of CNBDA that abolished mammosphere formation in the HER2-positive BT474 breast cancer cell line is 2-fold lower than the amount used in the MDA-MB468 cells, indicating that the more tyrosine kinase signaling dependent the cancer cell is the better its response to CNBDA.

In an embodiment of this invention, a compound that is 4,4'-(4'-Carboxy)-4-nonyloxy-[1,1'-biphenyl]-3,5-diyl) dibutanoic acid (abbreviated "CNBDA") having the following chemical structure:

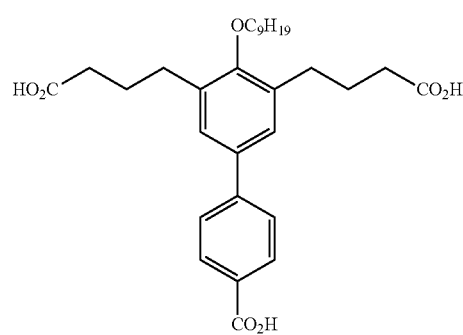

wherein the chemical structure has a biphenyl backbone having a lower positioned phenyl group that is attached to an upper positioned phenyl group, wherein a carboxylate group is attached to the lower phenyl group, and two butyric acid groups each attached at different positions to the upper phenyl group, and a nonyloxy group attached to the upper phenyl group at a position between each of the butyric acid groups attached to the upper phenyl group, is provided.

In another embodiment of this invention, one or more derivatives of the above described compound CNBDA is provided wherein the derivative compound has one or more of the following substitutions (a) replacement of one or both of the butyric acid groups of the CNBDA compound with an organic acid group (carboxylic group) having from 1-3 carbon atoms in chain length, or having from 5 to 30, or more carbon atoms in chain length, wherein the carbon atom chains are either saturated, partially saturated, or unsaturated with respect to the carbon to carbon bonding of the carbon atom chain, (b) replacement of the carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty, or more carbon atoms in chain length.

In another embodiment of this invention, a compound is provided having the chemical formula II:

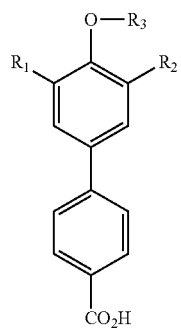

wherein $R_1$ and $R_2$ are the same or different and are independently selected from the group of (a) an organic acid group (carboxylic group) having from 1-30 or more carbon atoms in chain length, wherein the carbon atom chains are either saturated, partially saturated, or unsaturated with respect to the carbon to carbon bonding of the carbon atom chain, and (b) replacement of the carboxylic groups of (a) with a phosphate, a sulphate, an amide, an hydroxyl, an aldehyde, or a halide group, and wherein $R_3$ is an alkane group having from one to thirty or more carbon atoms in chain length.

Another embodiment of this invention provides a pharmaceutical composition comprising a compound of the chemical formula:

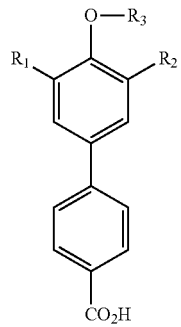

wherein $R_1$ and $R_2$ are the same or different and are independently selected from the group of (a) an organic acid group (carboxylic group) having from 1-30 or more carbon atoms in chain length, wherein the carbon atom chains are either saturated, partially saturated, or unsaturated with respect to the carbon to carbon bonding of the carbon atom chain, and (b) replacement of the carboxylic groups of (a) with a phosphate, a sulphate, an amide, an hydroxyl, an aldehyde, or a halide group, and wherein $R_3$ is an alkane group having from one to thirty or more carbon atoms in chain length, and a pharmaceutically acceptable carrier. The pharmaceutical composition includes wherein the pharmaceutically acceptable carrier is any pharmaceutical carrier that is known by those skilled in the art, and specifically includes but is not limited to a pharmaceutical carrier that is selected from the group consisting of dextrose, water, saline, isotonic saline, and lactose.

In another embodiment of this invention, a pharmaceutical composition comprising a compound that is 4,4'-(4'-Carboxy)-4-nonyloxy-[1,1'-biphenyl]-3,5-diyl)dibutanoic acid (abbreviated "CNBDA") having the following chemical structure:

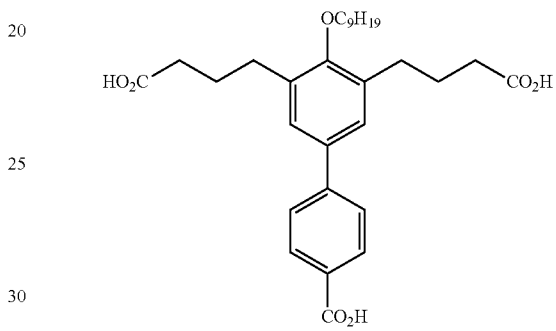

wherein said chemical structure has a biphenyl backbone having a lower positioned phenyl group that is attached to an upper positioned phenyl group, wherein a carboxylate group is attached to said lower phenyl group, and two butyric acid groups each attached at different positions to said upper phenyl group, and a nonyloxy group attached to said upper phenyl group at a position between each of said butyric acid groups, and a pharmaceutically acceptable carrier. The pharmaceutical composition as described herein includes wherein the compound is a derivative of CNBNA wherein the derivative compound has one or more of the following substitutions (a) replacement of one or both of said butyric acid groups of the CNBDA compound with an organic acid group (carboxylic group) having from 1-3 carbon atoms in chain length, or having from 5 to 30, or more carbon atoms in chain length, wherein the carbon atom chains are either saturated, partially saturated, or unsaturated with respect to the carbon to carbon bonding of said carbon atom chain, (b) replacement of said carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty, or more carbon atoms in chain length. The pharmaceutical composition includes pharmaceutically acceptable carriers as described herein.

In yet another embodiment of this invention, a method to inhibit SHP2 function is provided, comprising subjecting a cell culture to an effective amount of a compound that is 4,4'-(4'-Carboxy)-4-nonyloxy-[1,1'-biphenyl]-3,5-diyl) dibutanoic acid (abbreviated "CNBDA") having the following chemical structure:

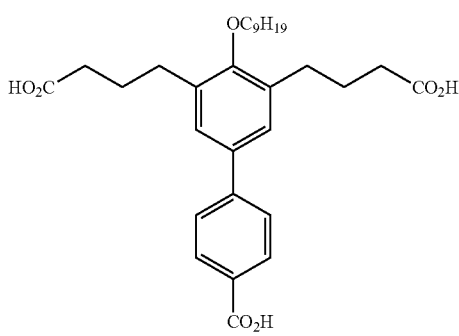

wherein the chemical structure has a biphenyl backbone having a lower positioned phenyl group that is attached to an upper positioned phenyl group, wherein a carboxylate group is attached to the lower phenyl group, and two butyric acid groups each attached at different positions to the upper phenyl group, and a nonyloxy group attached to the upper phenyl group at a position between the two butyric acid groups, for inhibiting SHP2 function. Another embodiment of this invention discloses the method as described herein for inhibiting SHP2 function, comprising subjecting the cell culture to one or more derivatives of the compound CNBDA wherein the derivative compound has one or more of the following substitutions (a) replacement of one or both of the butyric acid groups of the CNBDA compound with an organic acid group (carboxylic group) having from 1-3 carbon atoms in chain length, or having from 5 to 30, or more carbon atoms in chain length, wherein the carbon atom chains are either saturated, partially saturated, or unsaturated with respect to the carbon to carbon bonding of the carbon atom chain, (b) replacement of the carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty, or more carbon atoms in chain length.

Another embodiment of this invention provides a method to treat a patient with cancer comprising administering to a patient an effective amount of a compound comprising 4,4'-(4'-Carboxy)-4-nonyloxy-[1,1'-biphenyl]-3,5-diyl) dibutanoic acid (abbreviated "CNBDA") having the following chemical structure:

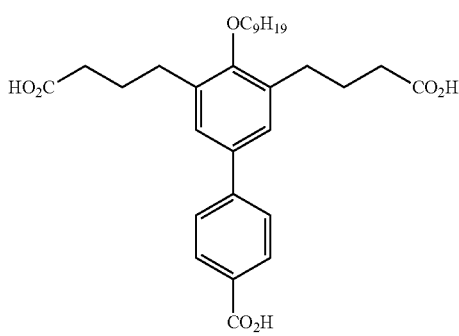

wherein the chemical structure has a biphenyl backbone having a lower positioned phenyl group that is attached to an upper positioned phenyl group, wherein a carboxylate group is attached to the lower phenyl group, and two butyric acid groups wherein each butyric acid group is attached at different positions to the upper phenyl group, and a nonyloxy group attached to the upper phenyl group at a position between each of the butyric acid groups, for treating the patient with cancer. In a preferred embodiment of this invention, the method for treating a patient with cancer, as described herein, includes wherein the cancer is a HER2-positive BT474 cancer cell line or a EGFR-amplified MDA-MB468 cancer cell line. In another preferred embodiment of this invention, the method for treating a patient with cancer, as described herein, includes administering to the patient an effective amount of one or more derivatives of the compound CNBDA wherein the derivative compound has one or more of the following substitutions (a) replacement of one or both of the butyric acid groups of the CNBDA compound with an organic acid group (carboxylic group) having from 1-3 carbon atoms in chain length, or having from 5 to 30, or more carbon atoms in chain length, wherein the carbon atom chains are either saturated, partially saturated, or unsaturated with respect to the carbon to carbon bonding of the carbon atom chain, (b) replacement of the carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty, or more carbon atoms in chain length, for treating the patient. In another preferred embodiment of this invention, as described herein, the cancer is a HER2-positive BT474 cancer cell line or a EGFR-amplified MDA-MB468 cancer cell line.

Another embodiment of this invention provides a method of making 4,4'-(4'-Carboxy)-4-nonyloxy-[1,1'-biphenyl]-3,5-diyl)dibutanoic acid (abbreviated "CNBDA") comprising adding a solution of lithium hydroxide monohydrate (1.02 g, 25 mmol, 14.7 equiv) in water (25 mL) to a solution of compound 4,4'-(4'-Carboxy)-4-nonyloxy-[1,1'-biphenyl]-3,5-diyl)dibutanoic acid, mixture of methyl and ethyl esters (0.97 g, ~1.70 mmol, 1.0 equivalent) in tetrahydrofuran (25 mL) to form a mixture, stirring the mixture at room temperature for a time period to complete the reaction of the aforementioned lithium hydroxide monohydrate and 4,4'-(4'-Carboxy)-4-nonyloxy-[1,1'-biphenyl]-3,5-diyl)dibutanoic acid mixture of methyl and ethyl esters, concentrating the mixture under reduced pressure to remove the tetrahydrofuran to form a residual aqueous solution, cooling the aqueous residual solution and making the aqueous residual solution acidic to form a precipitate in an aqueous suspension, extracting the aqueous suspension with a 10:1 mixture of ethyl acetate and tetrahydrofuran to form an organic phase, washing the organic phase with saturated brine to form a washed organic phase, and drying the washed organic phase over sodium sulfate to form a filtrate, concentrating the filtrate under reduced pressure to form a solid, and drying the solid in a vacuum to yield the CNBDA.

REFERENCES

1. Feng G S, Hui C C, Pawson T: SH2-containing phosphotyrosine phosphatase as a target of protein-tyrosine kinases. *Science* 1993, 259(5101):1607-1611.

2. Hof P, Pluskey S, Dhe-Paganon S, Eck M J, Shoelson S E: Crystal structure of the tyrosine phosphatase SHP-2. *Cell* 1998, 92(4):441-450.

3. Bennett A M, Hausdorff S F, O'Reilly A M, Freeman R M, Neel B G: Multiple requirements for SHPTP2 in epidermal growth factor-mediated cell cycle progression. *Molecular and cellular biology* 1996, 16(3):1189-1202.

4. Feng G S, Shen R, Heng H H, Tsui L C, Kazlauskas A, Pawson T: Receptor-binding, tyrosine phosphorylation and chromosome localization of the mouse SH2-containing phosphotyrosine phosphatase Syp. *Oncogene* 1994, 9(6):1545-1550.

5. Saxton T M, Ciruna B G, Holmyard D, Kulkarni S, Harpal K, Rossant J, Pawson T: The SH2 tyrosine phosphatase shp2 is required for mammalian limb development. *Nature genetics* 2000, 24(4):420-423.

6. Saxton T M, Henkemeyer M, Gasca S, Shen R, Rossi D J, Shalaby F, Feng G S, Pawson T: Abnormal mesoderm patterning in mouse embryos mutant for the SH2 tyrosine phosphatase Shp-2. *The EMBO journal* 1997, 16(9):2352-2364.

7. O'Reilly A M, Pluskey S, Shoelson S E, Neel B G: Activated mutants of SHP-2 preferentially induce elongation of Xenopus animal caps. *Molecular and cellular biology* 2000, 20(4299-311.

8. Tartaglia M, Martinelli S, Iavarone I, Cazzaniga G, Spinelli M, Giarin E, Petrangeli V, Carta C, Masetti R, Arico M et al: Somatic PTPN11 mutations in childhood acute myeloid leukaemia. *British journal of haematology* 2005, 129(3):333-339.

9. Tartaglia M, Mehler E L, Goldberg R, Zampino G, Brunner H G, Kremer H, van der Burgt I, Crosby A H, Ion A, Jeffery S et al: Mutations in PTPN11, encoding the protein tyrosine phosphatase SHP-2, cause Noonan syndrome. *Nature genetics* 2001, 29(4):465-468.

10. Tartaglia M, Niemeyer C M, Fragale A, Song X, Buechner J, Jung A, Hahlen K, Hasle H, Licht J D, Gelb B D: Somatic mutations in PTPN11 in juvenile myelomonocytic leukemia, myelodysplastic syndromes and acute myeloid leukemia. *Nature genetics* 2003, 34(2):148-150.

11. Cunnick J M, Dorsey J F, Munoz-Antonia T, Mei L, Wu J: Requirement of SHP2 binding to Grb2-associated binder-1 for mitogen-activated protein kinase activation in response to lysophosphatidic acid and epidermal growth factor. *The Journal of biological chemistry* 2000, 275(18):13842-13848.

12. Hadari Y R, Kouhara H, Lax I, Schlessinger J: Binding of Shp2 tyrosine phosphatase to FRS2 is essential for fibroblast growth factor-induced PC12 cell differentiation. *Molecular and cellular biology* 1998, 18(7):3966-3973.

13. Kuhne M R, Pawson T, Lienhard G E, Feng G S: The insulin receptor substrate 1 associates with the SH2-containing phosphotyrosine phosphatase Syp. *The Journal of biological chemistry* 1993, 268(16):11479-11481.

14. Lechleider R J, Sugimoto S, Bennett A M, Kashishian A S, Cooper J A, Shoelson S E, Walsh C T, Neel B G: Activation of the SH2-containing phosphotyrosine phosphatase SH-PTP2 by its binding site, phosphotyrosine 1009, on the human platelet-derived growth factor receptor. *The Journal of biological chemistry* 1993, 268(29):21478-21481. 16

15. Schaeper U, Gehring N H, Fuchs K P, Sachs M, Kempkes B, Birchmeier W: Coupling of Gab1 to c-Met, Grb2, and Shp2 mediates biological responses. *The Journal of cell biology* 2000, 149(7):1419-1432.

16. Tomic S, Greiser U, Lammers R, Kharitonenkov A, Imyanitov E, Ullrich A, Bohmer F D: Association of SH2 domain protein tyrosine phosphatases with the epidermal growth factor receptor in human tumor cells. Phosphatidic acid activates receptor dephosphorylation by PTP1C. *The Journal of biological chemistry* 1995, 270(36):21277-21284.

17. Bentires-Alj M, Paez J G, David F S, Keilhack H, Halmos B, Naoki K, Maris J M, Richardson A, Bardelli A, Sugarbaker D J et al: Activating mutations of the noonan syndrome-associated SHP2/PTPN11 gene in human solid tumors and adult acute myelogenous leukemia. *Cancer research* 2004, 64(24):8816-8820.

18. Mohi M G, Williams I R, Dearolf C R, Chan G, Kutok J L, Cohen S, Morgan K, Boulton C, Shigematsu H, Keilhack H et al: Prognostic, therapeutic, and mechanistic implications of a mouse model of leukemia evoked by Shp2 (PTPN11) mutations. *Cancer cell* 2005, 7(2):179-191.

19. Araki T, Mohi M G, Ismat F A, Bronson R T, Williams I R, Kutok J L, Yang W, Pao L I, Gilliland D G, Epstein J A et al: Mouse model of Noonan syndrome reveals cell type- and gene dosage-dependent effects of Ptpnll mutation. *Nature medicine* 2004, 10(8):849-857.

20. Flint A J, Tiganis T, Barford D, Tonks N K: Development of " substrate-trapping" mutants to identify physiological substrates of protein tyrosine phosphatases. *Proceedings of the National Academy of Sciences of the United States of America* 1997, 94(5):1680-1685.

21. Merritt R, Hayman M J, Agazie Y M: Mutation of Thr466 in SHP2 abolishes its phosphatase activity, but provides a new substrate-trapping mutant. *Biochimica et biophysica acta* 2006, 1763(1):45-56.

22. Frearson J A, Alexander D R: The phosphotyrosine phosphatase SHP-2 participates in a multimeric signaling complex and regulates T cell receptor (TCR) coupling to the Ras/mitogen-activated protein kinase (MAPK) pathway in Jurkat T cells. *The Journal of experimental medicine* 1998, 187(9):1417-1426.

23. Feng G S, Pawson T: Phosphotyrosine phosphatases with SH2 domains: regulators of signal transduction. *Trends Genet* 1994, 10(2):54-58.

24. Agazie Y M, Hayman M J: Molecular mechanism for a role of SHP2 in epidermal growth factor receptor signaling. *Mol Cell Biol* 2003, 23(21):7875-7886.

25. Zhou X, Agazie Y M: Molecular mechanism for SHP2 in promoting HER2-induced signaling and transformation. *The Journal of biological chemistry* 2009, 284(18):12226-12234.

26. Burks J, Agazie Y M: Modulation of alpha-catenin Tyr phosphorylation by SHP2 positively effects cell transformation induced by the constitutively active FGFR3. *Oncogene* 2006, 25(54):7166-7179.

27. Zhang S Q, Yang W, Kontaridis M I, Bivona T G, Wen G, Araki T, Luo J, Thompson J A, Schraven B L, Philips M R et al: Shp2 regulates SRC family kinase activity and Ras/Erk activation by controlling Csk recruitment. *Molecular cell* 2004, 13(3):341-355.

28. Agazie Y M, Movilla N, Ischenko I, Hayman M J: The phosphotyrosine phosphatase SHP2 is a critical mediator of transformation induced by the oncogenic fibroblast growth factor receptor 3. *Oncogene* 2003, 22(44):6909-6918. 17

29. Hakak Y, Hsu Y S, Martin G S: Shp-2 mediates v-Src-induced morphological changes and activation of the anti-apoptotic protein kinase Akt. *Oncogene* 2000, 19(28):3164-3171.

30. Aceto N, Sausgruber N, Brinkhaus H, Gaidatzis D, Martiny-Baron G, Mazzarol G, Confalonieri S, Quarto M, Hu G, Balwierz P J et al: Tyrosine phosphatase SHP2 promotes breast cancer progression and maintains tumor-initiating cells via activation of key transcription factors and a positive feedback signaling loop. *Nature medicine* 2012, 18(4):529-537.

31. Ren Y, Chen Z, Chen L, Fang B, Win-Piazza H, Haura E, Koomen J M, Wu J: Critical role of Shp2 in tumor growth involving regulation of c-Myc. *Genes & cancer* 2010, 1(10):994-1007.

32. Zhou X D, Agazie Y M: Inhibition of SHP2 leads to mesenchymal to epithelial transition in breast cancer cells. *Cell death and differentiation* 2008, 15(6):988-996.

33. Deb T B, Wong L, Salomon D S, Zhou G, Dixon J E, Gutkind J S, Thompson S A, Johnson G R: A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation. *The Journal of biological chemistry* 1998, 273(27):16643-16646.

34. Ahmed Z, George R, Lin C C, Suen K M, Levitt J A, Suhling K, Ladbury J E: Direct binding of Grb2 SH3 domain to FGFR2 regulates SHP2 function. *Cellular signalling* 2010, 22(1):23-33.

35. Ahmed Z, Lin C C, Suen K M, Melo F A, Levitt J A, Suhling K, Ladbury J E: Grb2 controls phosphorylation of FGFR2 by inhibiting receptor kinase and Shp2 phosphatase activity. *The Journal of cell biology* 2013, 200(4):493-504.

36. Li J, Reed S A, Johnson S E: Hepatocyte growth factor (HGF) signals through SHP2 to regulate primary mouse myoblast proliferation. *Experimental cell research* 2009, 315(13):2284-2292.

37. Mali R S, Ma P, Zeng L F, Martin H, Ramdas B, He Y, Sims E, Nabinger S, Ghosh J, Sharma N et al: Role of SHP2 phosphatase in KIT-induced transformation: identification of SHP2 as a druggable target in diseases involving oncogenic KIT. *Blood* 2012, 120(13):2669-2678.

38. Miura K, Wakayama Y, Tanino M, Orba Y, Sawa H, Hatakeyama M, Tanaka S, Sabe H, Mochizuki N: Involvement of EphA2-mediated tyrosine phosphorylation of Shp2 in Shp2-regulated activation of extracellular signal-regulated kinase. *Oncogene* 2013.

39. Muenst S, Obermann E C, Gao F, Oertli D, Viehl C T, Weber W P, Fleming T, Gillanders W E, Soysal S D: Src homology phosphotyrosyl phosphatase-2 expression is an independent negative prognostic factor in human breast cancer. *Histopathology* 2013, 63(1):74-82.

40. Zhou X, Coad J, Ducatman B, Agazie Y M: SHP2 is up-regulated in breast cancer cells and in infiltrating ductal carcinoma of the breast, implying its involvement in breast oncogenesis. *Histopathology* 2008, 53(4):389-402.

41. Hara M, Nakanishi H, Tsujimura K, Matsui M, Yatabe Y, Manabe T, Tatematsu M: Interleukin-2 potentiation of cetuximab antitumor activity for epidermal growth factor receptor-overexpressing gastric cancer xenografts through antibody-dependent cellular cytotoxicity. *Cancer science* 2008, 99(7):1471-1478.

42. Hognason T, Chatterjee S, Vartanian T, Ratan R R, Ernewein K M, Habib A A: Epidermal growth factor receptor induced apoptosis: potentiation by inhibition of Ras signaling. *FEBS letters* 2001, 491(1-2):9-15. 18

43. Morris G M, Huey R, Lindstrom W, Sanner M F, Belew R K, Goodsell D S, Olson A J: AutoDock4 and AutoDockTools4: Automated docking with selective receptor flexibility. *J Comput Chem* 2009, 30(16):2785-2791.

44. Ciardiello F, Caputo R, Bianco R, Damiano V, Pomatico G, De Placido S, Bianco A R, Tortora G: Antitumor effect and potentiation of cytotoxic drugs activity in human cancer cells by ZD-1839 (Iressa), an epidermal growth factor receptor-selective tyrosine kinase inhibitor. *Clinical cancer research: an official journal of the American Association for Cancer Research* 2000, 6(5):2053-2063.

45. Maa M C, Leu T H, McCarley D J, Schatzman R C, Parsons S J: Potentiation of epidermal growth factor receptor-mediated oncogenesis by c-Src: implications for the etiology of multiple human cancers. *Proceedings of the National Academy of Sciences of the United States of America* 1995, 92(15):6981-6985.

46. Bentires-Alj M, Gil S G, Chan R, Wang Z C, Wang Y, Imanaka N, Harris L N, Richardson A, Neel B G, Gu H: A role for the scaffolding adapter GAB2 in breast cancer. *Nature medicine* 2006, 12(1):114-121.

47. Debnath J, Muthuswamy S K, Brugge J S: Morphogenesis and oncogenesis of MCF-10A mammary epithelial acini grown in three-dimensional basement membrane cultures. *Methods* 2003, 30(3):256-268.

48. Engelmann K, Shen H, Finn O J: MCF7 side population cells with characteristics of cancer stem/progenitor cells express the tumor antigen MUC1. *Cancer Res* 2008, 68(7):2419-2426.

49. Fillmore C M, Kuperwasser C: Human breast cancer cell lines contain stem-like cells that self-renew, give rise to phenotypically diverse progeny and survive chemotherapy. *Breast cancer research: BCR* 2008, 10(2):R25

It will be appreciated by those persons skilled in the art that changes could be made to the embodiments described herein without departing from the broad inventive concept thereof. It is understood, therefore, that this invention is not limited to the particular embodiments disclosed, but is intended to cover modifications that are within the spirit and scope of the invention, as defined by the appended claims.

We claim:

1. A compound that is 4,4'-(4'-Carboxy)-4-nonyloxy-[1,1'-biphenyl]-3,5-diyl)dibutanoic acid (abbreviated "CNBDA") having the following chemical structure:

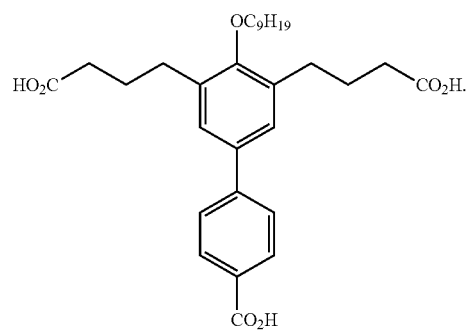

2. A compound that is a derivative of 4,4'-(4'-Carboxy)-4-nonyloxy-[1,1'-biphenyl]-3,5-diyl)dibutanoic acid (abbreviated "CNBDA") having the following chemical structure:

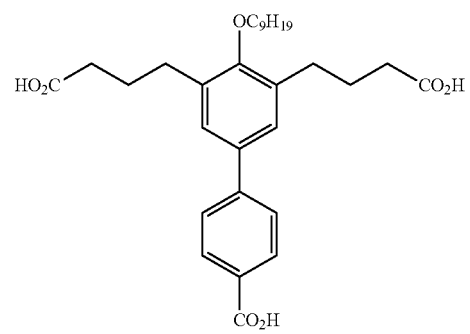

wherein said derivative compound has one or more of the following substitutions (a) replacement of one or both of said butyric acid groups of the CNBDA compound with an organic acid group (carboxylic group) having from 1-3 carbon atoms in chain length, or having from 5 to 30 carbon atoms in chain length, wherein the carbon atom chains are either saturated, partially saturated, or unsaturated with respect to the carbon to carbon bonding of said carbon atom chain, (b) replacement of said carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty carbon atoms in chain length.

3. A compound of the chemical formula:

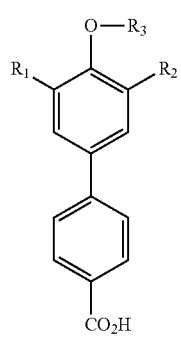

wherein $R_1$ and $R_2$ are the same or different and are independently selected from the group of (a) an organic acid group (carboxylic group) having from 1-30 carbon atoms in chain length, wherein organic acid group is not a cyclic organic acid, wherein the carbon atom chains are either saturated, partially saturated, or unsaturated with respect to the carbon to carbon bonding of the carbon atom chain, and (b) replacement of the carboxylic groups of (a) with a phosphate, a sulphate, an amide, an hydroxyl, an aldehyde, or a halide group, and wherein $R_3$ is an alkyl group having from one to thirty carbon atoms in chain length.

4. A pharmaceutical composition comprising a compound of the chemical formula:

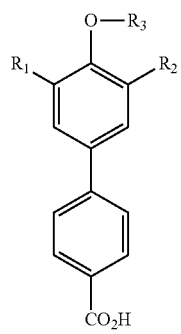

wherein $R_1$ and $R_2$ are the same or different and are independently selected from the group of (a) an organic acid group (carboxylic group) having from 1-30 carbon atoms in chain length, wherein the carbon atom chains are either saturated, partially saturated, or unsaturated with respect to the carbon to carbon bonding of the carbon atom chain, and (b) replacement of the carboxylic groups of (a) with a phosphate, a sulphate, an amide, an hydroxyl, an aldehyde, or a halide group, and wherein $R_3$ is an alkyl group having from one to thirty carbon atoms in chain length, and a pharmaceutically acceptable carrier.

5. The pharmaceutical composition of claim 4 wherein said pharmaceutically acceptable carrier is selected from the group consisting of dextrose, water, saline, isotonic saline, and lactose.

6. A pharmaceutical composition comprising a compound that is 4,4'-(4'-Carboxy)-4-nonyloxy-[1, 1'-biphenyl]-3,5-diyl)dibutanoic acid (abbreviated "CNBDA") having the following chemical structure:

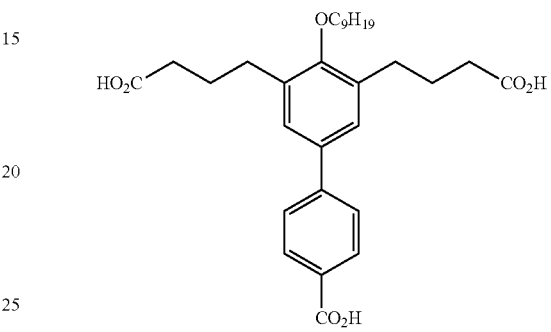

and a pharmaceutically acceptable carrier.

7. A pharmaceutical composition that is a derivative of 4,4'-(4'-Carboxy)-4-nonyloxy-[1, 1'-biphenyl]-3,5-diyl) dibutanoic acid (abbreviated "CNBDA") having the following chemical structure:

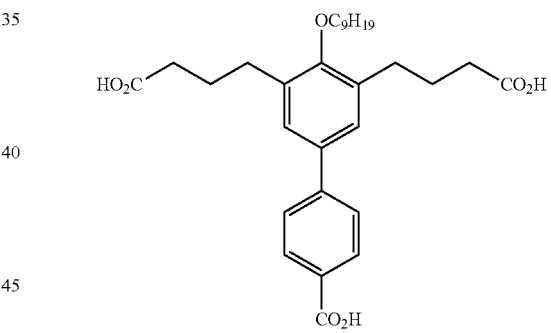

wherein said derivative compound has one or more of the following substitutions (a) replacement of one or both of said butyric acid groups of the CNBDA compound with an organic acid group (carboxylic group) having from 1-3 carbon atoms in chain length, or having from 5 to 30 carbon atoms in chain length, wherein the carbon atom chains are either saturated, partially saturated, or unsaturated with respect to the carbon to carbon bonding of said carbon atom chain, (b) replacement of said carboxylic groups with phosphate, sulphate, amide, hydroxyl, aldehyde, or halide groups, and (c) replacement of the nonane group with a carbon chain length having from 1-8 carbon atoms, or with a carbon chain length of ten to thirty carbon atoms in chain length.

8. The pharmaceutical composition of claim 6 wherein said pharmaceutically acceptable carrier is selected from the group consisting of dextrose, water, saline, isotonic saline, and lactose.

9. The pharmaceutical composition of claim 7 wherein said pharmaceutically acceptable carrier is selected from the group consisting of dextrose, water, saline, isotonic saline, and lactose.

* * * * *